United States Patent
Fuchs et al.

(10) Patent No.: US 12,188,004 B2
(45) Date of Patent: *Jan. 7, 2025

(54) CANCER IMMUNOTHERAPY USING TRANSFUSIONS OF ALLOGENEIC, TUMOR-SPECIFIC CD4+ T CELLS

(71) Applicant: The Johns Hopkins University, Baltimore, MD (US)

(72) Inventors: Ephraim Joseph Fuchs, Owings Mills, MD (US); Heather Jill Symons, Annapolis, MD (US); Lode Swinnen, Lutherville, MD (US)

(73) Assignee: The Johns Hopkins University, Baltimore, MD (US)

( * ) Notice: Subject to any disclaimer, the term of this patent is extended or adjusted under 35 U.S.C. 154(b) by 755 days.

This patent is subject to a terminal disclaimer.

(21) Appl. No.: 16/786,761

(22) Filed: Feb. 10, 2020

(65) Prior Publication Data
US 2020/0163997 A1 May 28, 2020

Related U.S. Application Data

(63) Continuation-in-part of application No. 15/939,059, filed on Mar. 28, 2018, now abandoned, which is a continuation of application No. 14/398,724, filed as application No. PCT/US2013/032129 on Mar. 15, 2013, now Pat. No. 9,931,359.

(60) Provisional application No. 61/644,126, filed on May 8, 2012.

(51) Int. Cl.
*A61K 39/00* (2006.01)
*A61K 31/664* (2006.01)
*A61K 45/06* (2006.01)
*C12N 5/00* (2006.01)
*C12N 5/0783* (2010.01)

(52) U.S. Cl.
CPC .......... *C12N 5/0638* (2013.01); *A61K 31/664* (2013.01); *A61K 39/461* (2023.05); *A61K 39/4611* (2023.05); *A61K 39/4615* (2023.05); *A61K 39/4621* (2023.05); *A61K 39/4622* (2023.05); *A61K 39/46434* (2023.05); *A61K 39/464401* (2023.05); *A61K 39/464838* (2023.05); *A61K 45/06* (2013.01); *C12N 5/0087* (2013.01); *A61K 2239/26* (2023.05); *A61K 2239/31* (2023.05); *A61K 2239/38* (2023.05); *A61K 2239/48* (2023.05); *A61K 2239/55* (2023.05); *A61K 2239/57* (2023.05); *Y02A 50/30* (2018.01)

(58) Field of Classification Search
None
See application file for complete search history.

(56) References Cited

U.S. PATENT DOCUMENTS

| | | | |
|---|---|---|---|
| 7,361,332 B2 | 4/2008 | Granger et al. | |
| 2001/0006631 A1 | 7/2001 | Hiserodt et al. | |
| 2004/0096456 A1* | 5/2004 | Conti-Fine | C07K 14/755 530/324 |
| 2006/0188520 A1 | 8/2006 | Steinman et al. | |
| 2006/0286089 A1 | 12/2006 | Berenson et al. | |
| 2007/0122415 A1* | 5/2007 | Gupta | C07K 14/47 435/5 |
| 2007/0128629 A1 | 6/2007 | Hildebrand et al. | |
| 2011/0065187 A1* | 3/2011 | Cai | A61K 39/0008 435/348 |
| 2014/0134145 A1 | 5/2014 | Tu et al. | |
| 2014/0308305 A1* | 10/2014 | Franzusoff | A61P 31/10 424/185.1 |
| 2019/0336530 A1 | 11/2019 | June et al. | |

FOREIGN PATENT DOCUMENTS

| | | |
|---|---|---|
| WO | WO 2018/223101 | 12/2018 |
| WO | WO 2019/222760 | 11/2019 |
| WO | WO 2019/241306 | 12/2019 |

OTHER PUBLICATIONS

Onlamoon et al ( Asian Pac J Allergy Immunol 2013;31:99-105.*
Fonteneau et al., ( J of Immunolog.Method, 2001, v.258, pp. 111-126.*
Eto et al J of Urology, 2008, v.179, p. 37.*
Li et al., Blood, 2011, v.118, pp. 5965-5976.*
Williams et al ., J of Immunol, 1996,v.156,pp. 153-159.*
Giralt, Sergio et al.: "*CD8-Depleted Donor Lymphocyte Infusion as Treatment for Relapsed Chronic Myelogenous Leukemia After Allogeneic Bone Marrow Transplantation*"; Blood, Dec. 1, 1995, vol. 86, No. 11, pp. 4337-4343.
June, Carl H. et al.: "*T-Cell Proliferation Involving the CD28 Pathway Is Associated with Cyclosporine-Resistant Interleukin 2 Gene Expression*"; Molecular and Cellular Biology, Dec. 1987, vol. 7, No. 12, p. 4472-4481.
Levine, B. L. et al. "*Effects of CD28 costimulation on long-term proliferation of CD4+ T cells in the absence of exogenous feeder cells*"; J. Immunol, 1997; 159:5921-5930; http://www.jimmunol.org/content/159/12/5921.
Perez-Diez, Ainhoa et al.: "*CD4 cells can be more efficient at tumor rejection than CD8 cells*"; Blood, Jun. 15, 2007, vol. 109, No. 12, pp. 5346-5354.
Thomas Anna K. et al.: "*A Cell-Based Artificial Antigen-Presenting Cell Coated with Anti-CD3 and CD28 Antibodies Enables Rapid Expansion and Long-Term Growth of CD4 T Lymphocytes*"; Clinical Immunology, vol. 105, No. 3, December, pp. 259-272, 2002, doi:10.1006/clim.2002.5277.

(Continued)

*Primary Examiner* — Michail A Belyavskyi
(74) *Attorney, Agent, or Firm* — DLA Piper LLP (US)

(57) ABSTRACT

The invention provides methods and compositions for administration of allogeneic lymphocytes as an exogenous source of CD4+ T cell help for endogenous, tumor-reactive CD8+ T cells.

19 Claims, 8 Drawing Sheets

Specification includes a Sequence Listing.

(56) References Cited

OTHER PUBLICATIONS

Alyea et al., CD8+ cell depletion of donor lymphocyte infusions using cd8 monoclonal aritibody-coated high-density microparticles (CD8-HDM) after allogeneic hematopoietic stem cell transplantation: a pilot study, Bone Marrow Transplantation, vol. 34, May 10, 2004, pp. 123-128.
Alyea, E.P. et al.: "Toxicity and efficacy of defined doses of CD4(+) donor lymphocytes for treatment of relapse after allogeneic bone marrow transplant"; Blood, vol. 91, No. 10, May 15, 1998, pp. 3671-3680.
Ciurea et al., Donor-specific anti-HLA Abs and graft failure in matched unrelated donor hematopoietic stem cell transplantation, Blood, vol. 118, Oct. 3, 2011, pp. 5957-5964.
Dazzi et al., Adoptive Immunotherapy Following Allegeneic Bone Marrow Transplantation, Annu. Rev. Medicine, vol. 49, 1998, pp. 329-340.
European Search Report and Search Opinion Received for EP Application No. 16190858.7, mailed on Jan. 26, 2017, 9 pages.
Extended European Search Report dated Oct. 6, 2015, regarding EP 13788469.8.
Giralt et al., CD8-Depleted Donor Lymphocyte Infusion as Treatment for Relapsed Chronic Myelogenous Leukemia After Allogeneic Bone Marrow Transplantation, Blood., vol. 86, No. 11, Dec. 1, 1995, pp. 4337-4343.
International Preliminary Report on Patentability received for PCT Patent Application No. PCT/US2013/032129, mailed on Nov. 20, 2014, 13 pages.
International Search Report and Written Opinion received for PCT Patent Application No. PCT/US2013/032129, mailed on Jul. 22, 2013, 21 pages.
Lee et al., The Feasibility and Clinical Efficacy of In Vivo Adsorption of Isohemagglutinins with Fresh Frozen Plasma (FFP) Infusion in Major ABO-incompatible Allogeneic Stem Cell Transplantation, Korean J. Hematol. vol. 40, No. 4, Dec. 2005, pp. 254-260.
Luznik, L. et al: "HLA-Haploidentical Bone Marrow Transplantation for Hematologic Malignancies Using Nonmyeloablative Conditioning and High-Dose, Posttransplantation Cyclophosphamide"; Biol Blood Marrow Transplant, vol. 14, No. 6, Jun. 1, 2008, pp. 641-650.
Munchel, Ashley T. et al.: "Treatment of hematological malignancies with nonmyeloablative, HLA-haploidentical bone marrow transplantation and high dose, post-transplantation cyclophosphamide"; Best Practice & Research Clinical Haematology, vol. 24, No. 3, 2011, pp. 359-368.
Symons, H. J. et al.: "The Allogeneic Effect Revisited: Exogenous Help for Endogenous, Tumor-Specific T Cells"; Biology of Blood and Marrow Transplantation, vol. 14, No. 5, May 1, 2008, pp. 499-509.
Xie et al., "Naive tumor-specific CD4+ T cells differentiated iri vivo eradicate established melanoma", J. Exp. Med., vol. 207, No. 3, Mar. 15, 2010, pp. 651-667.
Jonges et al, "The Phenotypic Heterogeneity of Human Natural Killer Cells: Presence of at least 48 Different Subsets in the Peripheral Blood", Scand. J. Immunol., 53:103-110, 2001.
Parnes, "Molecular Biology and Function of CD4 and CD8", Advances in Immunology, 44:265-311, 1989.
Srour et al., "Cytolytic Activity of Human Natural Killer Cell Subpopulations Isolated by Four-Color Immunofluorescence Flow Cytometric Cell Sorting", Cytometry 11:442-446, 1990.
Meyer, Ralph G. et al.: "*Prophylactic transfer of CD8-depleted donor lymphocytes after T-cell-depleted reduced-intensity transplantation*"; Blood, Jan. 1, 2007, vol. 109, No. 1, pp. 374-382.
PCT International Search Report and Written Opinion in International Application No. PCT/US2021/017279, dated Apr. 29, 2021, 16 pages.

\* cited by examiner

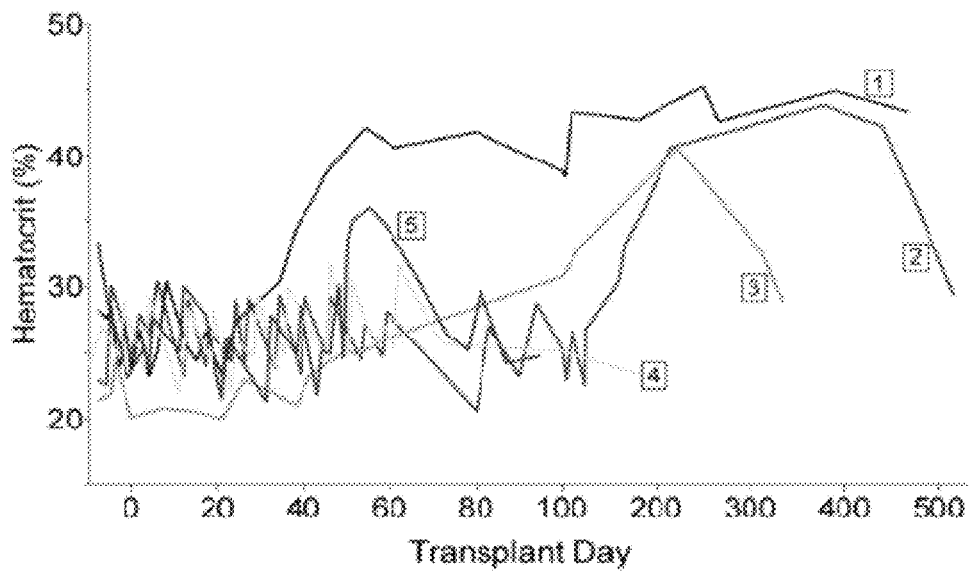

Figure 1. Hematocrit values in MDS patients experiencing graft rejection following non-myeloablative conditioning and transplantation of marrow from partially HLA-mismatched relatives.

FIG. 1

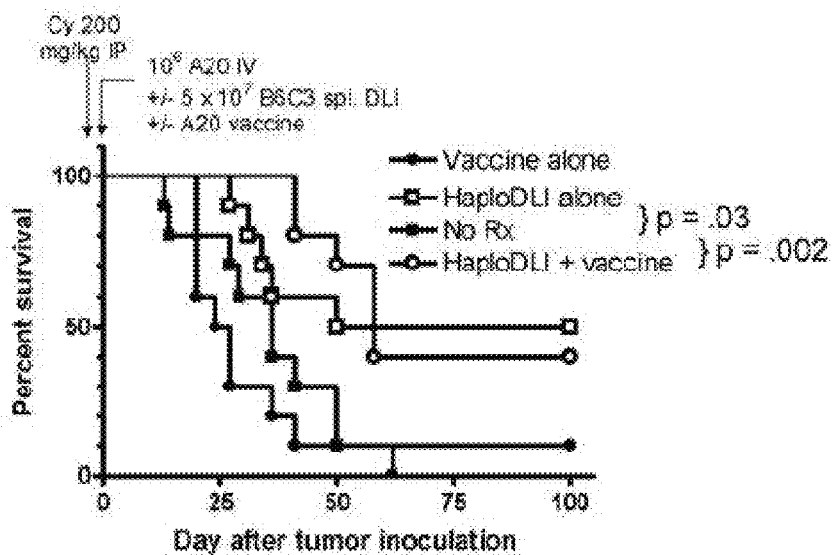

Figure 2. Non-engrafting DLI induces anti-tumor immunity. BALB/c x C57BL/6 $F_1$ mice (H-$2^{b/d}$; n=10/group) were conditioned with Cy 200 mg/kg IP on day -1. On day 0, they received $10^6$ A20 lymphoma cells IV +/- 5 x $10^7$ spleen cells from partially MHC-mismatched B6 x C3H F1 donors (H-$2^{b/k}$) +/- autologous tumor cell vaccine sc ($10^6$ irradiated A20 + 2 x $10^5$ irr. B78H1-GM-CSF).

CANCER IMMUNOTHERAPY USING TRANSFUSIONS OF ALLOGENEIC, TUMOR-SPECIFIC CD4+ T CELLS

CROSS-REFERENCE TO RELATED APPLICATIONS

This application is a continuation-in-part of U.S. application Ser. No. 15/939,059 filed Mar. 28, 2018, which is a continuation application of U.S. application Ser. No. 14/398,724 filed Nov. 3, 2014, now issued as U.S. Pat. No. 9,931,359; which is a 35 USC § 371 National Stage application of International Application No. PCT/US2013/032129 filed Mar. 15, 2013, which claims the benefit under 35 USC § 119(e) to U.S. Application Ser. No. 61/644,126 filed May 8, 2012. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under CA105148 and CA015396 awarded by the National Institutes of Health. The government has certain rights in the invention.

INCORPORATION OF SEQUENCE LISTING

The material in the accompanying sequence listing is hereby incorporated by reference into this application. The accompanying sequence listing text file, name JHU3680_3_Sequence_Listing.txt, was created on Feb. 10, 2020, and is 4 kb. The file can be assessed using Microsoft Word on a computer that uses Windows OS.

BACKGROUND OF THE INVENTION

Field of the Invention

The invention relates generally to immunology and more specifically, to methods and compositions containing allogeneic lymphocytes to treat cancer.

Background Information

The immune system of a host provides the means for quickly and specifically mounting a protective response to pathogenic microorganisms and also for contributing to rejection of malignant tumors. Immune responses have been generally described as including humoral responses, in which antibodies specific for antigens are produced by differentiated B lymphocytes, and cell mediated responses, in which various types of T lymphocytes eliminate antigens by a variety of mechanisms. For example, CD4 (also called CD4+) helper T cells that are capable of recognizing specific antigens may respond by releasing soluble mediators such as cytokines to recruit additional cells of the immune system to participate in an immune response. CD8 (also called CD8+) cytotoxic T cells are also capable of recognizing specific antigens and may bind to and destroy or damage an antigen-bearing cell or particle. In particular, cell mediated immune responses that include a cytotoxic T lymphocyte (CTL) response can be important for elimination of tumor cells and cells infected by a microorganism, such as virus, bacteria, or parasite.

Cancer includes a broad range of diseases and affects approximately one in four individuals worldwide. A CTL response is a key feature of effective cancer vaccines; effective CD4 T cell help plays a critical role in sustaining the cytotoxic activity of CD8 T cells and thus provides clinical benefit.

With respect to microbial infections, malaria, tuberculosis, HIV-AIDS and other viral infections, such as Epstein-Barr virus, Hepatitis B and C viruses, Herpes Simplex Virus (HSV) infections, and human papillomavirus (HPV), continue to contribute to global health concerns. It is estimated that viruses cause approximately 15% of all human cancers. Human papillomavirus, including both oncogenic and non-oncogenic serotypes, is the most common sexually transmitted infection in the world. While most immunocompetent individuals eliminate the virus, a fraction of healthy individuals fail to eliminate oncogenic strains of HPV, which then establish persistence in epithelial cells and can induce malignant transformation.

Emerging evidence suggests that cancers induce a state of unresponsiveness in lymphocytes that are specific for antigens uniquely expressed by the cancer. However, this unresponsiveness should be able to be reversed. Several human tumors are infiltrated by CD8+ T cells, and the degree of CD8+ T cell infiltration often correlates with absence of metastases and improved survival. However, these CD8+ T cells may not eliminate the cancer because of functional paralysis of tumor-specific CD4+ T cells.

Immunologic checkpoint inhibitors (CIs), including ipilimumab, nivolumab, and pembrolizumab, have been successful in the treatment of diverse cancers, which conclusively establishes that T cells of the immune system can cause tumors to regress resulting in prolonged survival and improved quality of life. However, the success of any cancer immunotherapy may be limited by T cell exhaustion, a phenomenon characterized by impaired proliferation, cytokine secretion, and killing capacity of tumor-specific T cells. Accordingly, there is significant interest in developing strategies to reverse T cell exhaustion in anti-cancer immunotherapy.

Recent evidence suggests that the CIs are unable to reverse T cell exhaustion. In contrast, allogeneic cell therapy, specifically an infusion of $CD4^+$ T cells from a major histocompatibility complex (MHC)-mismatched donor, was found capable of inducing the regression of advanced cancers that are resistant even to immunologic checkpoint blockade, even despite the eventual rejection of the donor cells. Depletion of $CD8^+$ cells from the donor lymphocytes abrogated the risks of sustained donor cell engraftment and fatal graft-versus-host disease (GVHD), without compromising anti-tumor efficacy of the infusion. When the donor and recipient are MHC-haploidentical to each other (as a parent is to a child or vice versa), vaccination of the donor against the E7 antigen of human papillomavirus (HPV) serotype 16 (HPV16) augmented the anti-tumor efficacy of CD8-depleted, non-engrafting donor lymphocyte infusion (NEDLI) against TC-1, an E7-expressing lung cancer. The anti-tumor efficacy of NEDLI from E7-primed donors could be augmented and recipients could be cured by culturing the primed cells, prior to infusion, with host- or donor-derived dendritic cells pulsed with peptides from E7 of HPV16. Mice that are cured of advanced TC-1 tumors by E7-primed NEDLI had no evidence of donor chimerism but contained an expanded population of host-derived, E7-specific memory CD4+ and CD8+ T cells, indicating that anti-tumor immunity had been imprinted onto the recipient by the NEDLI. These results demonstrate that a virus-induced tumor can be treated by the infusion of lymphocytes from a partially or fully HLA-matched donor that has been vaccinated against a viral antigen and suggest that it may be possible to treat sporadic tumors by giving lymphocytes from a donor vaccinated against a tumor neoantigen.

Further, mice cured of TC-1 by NEDLI resisted challenge with the same tumor, and spleen cells from the cured animals transferred anti-tumor immunity to TC-1-bearing, MHC-haploidentical recipients. Vaccination of a healthy donor against a tumor-specific antigen, and subsequent culture of the lymphocytes of the vaccinated donor with peptides derived from the tumor-specific antigen, can significantly augment the anti-tumor effect of non-engrafting donor lymphocyte infusion into an allogeneic recipient harboring the antigen-expressing tumor.

SUMMARY OF THE INVENTION

The present invention is based on the seminal discovery that infusion of allogeneic lymphocytes containing CD4+ T cells can break tolerance in host anti-tumor CD8+ T cells, even though the donor cells do not engraft long term in the recipient; and that an infusion of alloreactive and neoantigen-specific CD4+T cells can reverse exhaustion of endogenous, tumor-specific CD8+ T cells resulting in tumor regression. The present invention includes methods and compositions related to infusion of allogeneic, virus-specific and/or tumor neoantigen (neoAg)-specific CD4+T cells into subjects, having or prone to the development of cancer, for the purpose of reversing exhaustion of endogenous, tumor-specific CD8+ T cells resulting in tumor regression.

In one embodiment, the invention provides a method of making a lymphocyte composition including a) obtaining a peripheral blood cell composition from a donor, wherein the donor is optionally vaccinated against an antigen present in the recipient and wherein the peripheral blood cell composition comprises contains CD8+ T-cells, CD4+ T-cells and natural killer cells; b) depleting the peripheral blood cell composition of the CD8+ T-cells, wherein depleting the peripheral blood cell composition of the CD8+ T-cells is reducing the number of CD8+ T-cells in the peripheral blood cell composition by at least one order of magnitude; and c) expanding the CD4+ T cells specific to the antigen by culturing the CD4+ T cells with the antigen, wherein the donor is HLA-matched, partially HLA-matched, or HLA-haploidentical to the recipient, thereby making a lymphocyte composition.

In another embodiment, the invention provides a method of treating cancer in a subject including a) administering a lympho-depleting chemotherapy to the subject; and b) administering a lymphocyte cell composition to the subject, wherein the lymphocyte composition is obtained from a peripheral blood cell composition of an HLA-matched, partially HLA-mismatched, or HLA-haploidentical donor, wherein the donor is optionally vaccinated against a viral antigen and/or a tumor neoantigen present in the subject, wherein the composition is depleted of CD8+ T cells, and wherein the composition comprises an expanded population of CD4+ T cells specific to the viral and/or tumor neoantigen present in the subject. In one aspect, the partially HLA-matched or HLA-haploidentical donor has at least one human leukocyte antigen (HLA) Class II allele match relative to the recipient and the HLA Class II allele match is at a gene selected from the group consisting of HLA-DRB1, HLA-DQB1, and HLA-DPB1.

In an additional embodiment, the invention provides a cell bank including CD4+ T cells specific for a viral antigen, a tumor neoantigen, or a combination thereof, wherein the cell bank includes individual lines of CD4+ T cells, each line collected from a single donor of different human leukocyte antigen (HLA) types. In one aspect, the viral antigen is from HPV or Epstein Barr Virus.

BRIEF DESCRIPTION OF THE DRAWINGS

FIG. 1 shows the hematocrits of the five patients experiencing graft rejection after HLA-haploidentical bone marrow transplantation for myelodysplastic syndrome, with the jagged portions reflecting the effect of transfusion (graph).

FIG. 2 shows non-engrafting DLI induces anti-tumor immunity (graph).

FIG. 8A shows the percentage of CD8+ T cells that were reactive to the immunodominant, $H-2K^b$-restricted peptide of E7 as determined by staining with $H-2K-^b$ tetramers pulsed with the peptide in naïve B6C3 F1 mice. FIG. 8B shows the percentage of CD8+ T cells that were reactive to the immunodominant, $H-2K^b$-restricted peptide of E7 as determined by staining with $H-2K^b$ tetramers pulsed with the peptide in mice cured by haploDLI. FIG. 8C shows the percentage of CD8+ T cells that were reactive to the immunodominant, $H-2K^b$-restricted peptide of E7 as determined by staining with $H-2K^b$ tetramers pulsed with the peptide in mice cured by haploDLI, 14 days after TC-1 challenge. FIG. 8D shows the percentage of CD8+ T cells that were reactive to the immunodominant, $H-2K^b$-restricted peptide of E7 as determined by staining with $H-2K^b$ tetramers pulsed with the peptide in mice cured by haploDLI, 60 days after TC1 challenge. FIG. 8E shows cell surface expression of CD127 and PD-1 on the gated, E7-specific CD8+ T cells in the same condition at in FIG. 8A. FIG. 8F shows cell surface expression of CD127 and PD-1 on the gated, E7-specific CD8+ T cells in the same condition at in FIG. 8B. FIG. 8G shows cell surface expression of CD127 and PD-1 on the gated, E7-specific CD8+ T cells in the same condition at in FIG. 8C. FIG. 8H shows cell surface expression of CD127 and PD-1 on the gated, E7-specific CD8+ T cells in the same condition at in FIG. 8D.

DETAILED DESCRIPTION OF THE INVENTION

Figure 3A:
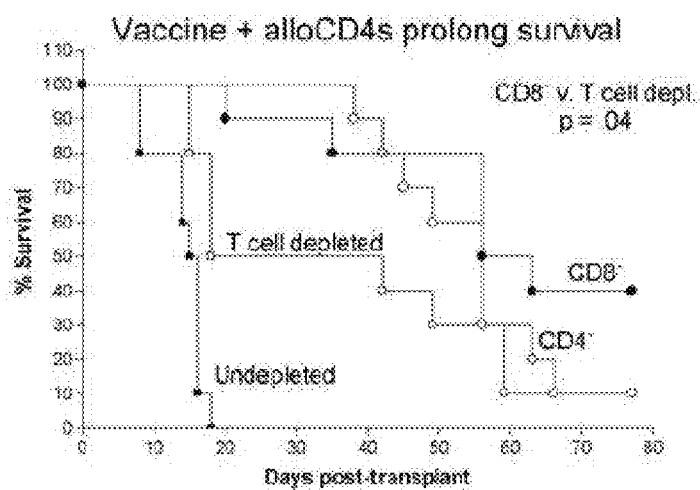
FIG. 3A shows engraftment of donor cells as vaccine plus alloCD4s prolong survival (graph).

The present disclosure arises at least in part from the seminal discovery that the immune response to cancer is hampered by functional defects of the patient's CD4+ T cells. Infusions of allogeneic lymphocytes can provide an exogenous source of CD4+ T cell help for endogenous, tumor-reactive CD8+ T cells. Depletion of CD8+ T cells from the donor lymphocyte infusion reduces the risk of sustained engraftment and graft-versus-host disease. Removal of regulatory T cells from the infused population may augment the ability of non-regulatory T cells to provide help for endogenous effectors of anti-tumor immunity. Allogeneic T cell therapy is typically given in the context of allogeneic stem cell transplantation, in which the patient receives highly immunosuppressive conditioning followed by an infusion of a stem cell graft containing unselected populations of mature T cells. In the treatment described here, the graft is engineered to minimize the possibility of sustained donor cell engraftment, and the anti-tumor effector T cells derive from the host. Thus, the therapy entails a unique cooperation of host and donor lymphocytes during the period of transient donor cell engraftment.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). Although any methods and materials similar or equivalent to those described herein can be used in the practice or testing of the invention, it will be understood that modifications and variations are encompassed within the spirit and scope of the instant disclosure. The preferred methods and materials are now described.

Administration of chemotherapy prior to the allogeneic cell infusion can augment the antitumor effect of the transiently engrafting lymphocytes, by promoting homeostatic expansion of the transferred lymphocytes, and/or by depleting host regulatory T cells and myeloid-derived suppressor cells. Infusions of allogeneic lymphocytes can provide an exogenous source of CD4+ T cell help for endogenous, tumor-reactive CD8+ T cells. Depletion of CD8+ T cells from the donor lymphocyte infusion reduces the risk of sustained engraftment and graft-versus-host disease. Removal of regulatory T cells from the infused population may augment the ability of non-regulatory T cells to provide help for endogenous effectors of anti-tumor immunity.

Allogeneic T cell therapy is typically given in the context of allogeneic stem cell transplantation, in which the patient receives highly immunosuppressive conditioning followed by an infusion of a stem cell graft containing unselected populations of mature T cells. The goal of alloSCT is to obtain sustained engraftment of the donor cells and entails the risk of mortality from graft-versus-host disease. In the treatment described here, the graft is engineered to minimize the possibility of sustained donor cell engraftment, and the anti-tumor effector T cells derive from the host. Thus the therapy entails a unique cooperation of host and donor lymphocytes during the period of transient donor cell engraftment.

This is a treatment that can be applied to any human or animal cancer. Variations of the present invention include: 1) variations of the chemotherapy regimen that is given prior to infusion of allogeneic lymphocytes (may include cyclophosphamide, fludarabine, 5-fluorouracil, gemcitabine, dasatinib, combinations thereof; 2) variations in the source of donor lymphocytes (may be from related or unrelated donors, may include defined mismatches at HLA Class I or Class II genetic loci; 3) variations in the types of cells selected for infusion, such as depletion of CD4+CD25+ regulatory T cells, depletion of CD8+ T cells. Donors may be immunized to defined antigens prior to lymphocyte infusions or may be polarized with cytokines or drugs ex vivo to enrich for Type I (IFN-gamma producing) or Type 17 (IL-17-producing) $CD4^+$ T cells.

$CD8^+$ T cells of the immune system can destroy cancer cells by recognizing tumor neoantigens, amino acid sequences that arise by mutation in the cancer cells and distinguish them from their healthy normal counterparts. However, cancers can avoid immune destruction by paralyzing the function of $CD4^+$ T cells whose "help" is required to prevent neoantigen-specific $CD8^+$ T cells from becoming exhausted. The allogeneic graft of the present invention can be used to reverse exhaustion of neoantigen-specific $CD8^+$ T cells and to restore the anti-cancer immune response by providing a fresh source of $CD4^+$ helper T cells from a healthy donor that has been vaccinated against a neoantigen from the patient's tumor.

In one embodiment, the invention provides a method of making an allogeneic lymphocyte composition for administration to a human recipient, comprising: vaccinating a human donor against an antigen present in the recipient; providing a peripheral blood cell composition from the human donor allogeneic to the recipient, the peripheral blood cell composition comprising a number of CD4+ T-cells, a number of CD8+ T-cells, and a number of natural killer cells, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, and (iii) the recipient does not have detectable antibodies reactive against human leukocyte antigens of the donor; and making the allogeneic lymphocyte composition from the peripheral blood cell composition by reducing the number of CD8+ T-cells in the peripheral blood cell composition by at least one order of magnitude, wherein the number of CD4+ T-cells in the allogeneic lymphocyte composition differs from the number of CD4+ T-cells in the peripheral blood cell composition by less than about 50%, and wherein the number of natural killer cells in the allogeneic lymphocyte composition is less than or equal to the number of natural killer cells in the peripheral blood cell composition.

The invention provides a method of making a lymphocyte composition to be administered to a recipient including a) obtaining a peripheral blood cell composition from a donor, wherein the donor is optionally vaccinated against an antigen present in the recipient and wherein the peripheral blood cell composition comprises contains CD8+ T-cells, CD4+ T-cells and natural killer cells; b) depleting the peripheral blood cell composition of the CD8+ T-cells, wherein depleting the peripheral blood cell composition of the CD8+ T-cells is reducing the number of CD8+ T-cells in the peripheral blood cell composition by at least one order of magnitude; and c) expanding the CD4+ T cells specific to the antigen by culturing the CD4+ T cells with the antigen, wherein the donor is HLA-matched. partially HLA-matched, or—haploidentical to the recipient, thereby making a lymphocyte composition. In one aspect, the partially HLA-matched or HLA-haploidentical donor has at least one human leukocyte antigen (HLA) Class II allele match relative to the recipient and the HLA Class II allele match at a gene selected from HLA-DRB1, HLA-DQB1, and/or HLA-DPB1.

Preferably, the donor and recipient are not the same human. The method includes providing a peripheral blood cell composition from a human donor allogeneic to the recipient, the peripheral blood cell composition comprising a number of CD4+ T-cells, a number of CD8+ T-cells, and a number of natural killer cells, some natural killer cells have CD8+ antigen and may be removed by the "reducing" step; however, preferred lymphocyte compositions of the present invention comprise at least some natural killer cells from the donor. In one aspect, (i) the donor comprises at least one human leukocyte antigen (HLA) Class II allele mismatch relative to the recipient in the donor versus the recipient direction (an HLA Class II allele mismatch in the donor versus recipient direction, "graft-versus-host direction) and the HLA Class II allele mismatch is at a gene such as HLA-DRB1, HLA-DQB1, or HLA-DPB1. The recipient does not have detectable antibodies reactive against human leukocyte antigens of the donor ("detectable antibodies" in this context are defined using standard methods of making this determination (for example, the recipient does not have antibodies against donor HLA molecules that are detectable by complement-dependent cytotoxicity, in flow cytometric cross-match assays a positive result is undesirable, or mean fluorescence intensity (MFI) of 3000 or greater in a solid phase immunoassay is unacceptable). In one aspect, the donor has at least one HLA Class II allele mis-match relative to the recipient in the donor anti-recipient (graft-versus-host) direction and the HLA Class II allele mis-match is at a gene selected from the group consisting of HLA-DRB1, HLA-DQB1, and HLA-DPB1.

"Expanding" a cell population of virus-specific or tumor neoantigen-specific T cells" refers to the generation of a lymphocyte population containing a higher frequency of T cells reactive to a virus or to a tumor neoantigen than is found in a healthy individual who has not been exposed to the virus or the tumor neoantigen.

The allogeneic lymphocyte composition is made from the peripheral blood cell composition by reducing the number of CD8+ T-cells in the peripheral blood cell composition by at least one order of magnitude, wherein (a) the number of CD4+ T-cells in the allogeneic lymphocyte composition differs from the number of CD4+ T-cells in the peripheral blood cell composition by less than about 50%. In a preferred embodiment, the ratio of the number of CD4+/the number of CD8+ T cells in the lymphocyte composition is preferably greater than or equal to about 30. Examples of some embodiments include, but are not limited to, the following doses per kilogram of recipient ideal body weight: a lymphocyte composition comprising $10^5$ CD4+ cells typically has no greater than $3.2 \times 10^3$ CD8+ cells, $10^6$ CD4+ cells typically has no greater than $3.2 \times 10^4$ CD8+ cells, $10^7$ CD4+ cells typically has no greater than $3.2 \times 10^5$ CD8+ cells, $10^8$ CD4+ cells typically has no greater than $3.2 \times 10^6$ CD8+ cells, and $5 \times 10^8$ CD4+ cells typically has no greater than $1.6 \times 10^7$ CD8+ cells.

The number of natural killer cells in the allogeneic lymphocyte composition is less than or equal to the number of natural killer cells in the peripheral blood cell composition. Reduced by one order of magnitude, preferably about two orders of magnitude, more preferably to about five orders of magnitude. In one embodiment, the number of CD8+ cells is reduced by about 2.5 orders of magnitude (e.g., using the magnetic bead cell sorter method).

By "depleted of CD8+ T cells" is meant having the number of CD8+ T cells, in a population of mixed cells, reduced by methods such as antibody against CD8 plus complement or by magnetic cell separation, such that the number of CD8+ T cells is at least 10-fold lower relative to other cells, such as CD4+ T cells, as compared to the undepleted population. As an example, if the ratio of CD4+ to CD8+ T cells in an undepleted peripheral blood population is 1.5:1, then the ratio of CD4+ to CD8+ T cells in a population that is depleted of CD8+ T cells is no less than 15:1.

As used herein, the term "vaccination" relates to the administration of a vaccine, a pharmaceutical preparation (pharmaceutical composition) or product that upon administration induces an immune response, in particular a cellular immune response, which can recognize and attack a pathogen or a diseased cell such as a cancer cell. A vaccine may be used for the prevention or treatment of a disease. The term "immune response" refers to an integrated bodily response to an antigen and preferably refers to a cellular immune response or a cellular as well as a humoral immune response. The immune response may be protective/preventive/prophylactic and/or therapeutic. Inducing an immune response" may mean that there was no immune response against a particular antigen before induction, but it may also mean that there was a certain level of immune response against a particular antigen before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor expressed antigen may be induced in a donor, which will help the recipient subject having a cancer disease to fight against the cancer disease. Inducing an immune response in this case may mean that the disease condition of the subject is ameliorated, that the subject does not develop metastases, or that the subject being at risk of developing a cancer disease does not develop a cancer disease.

In the present invention, "vaccination against a tumor-antigen" concerns a particular donor subject, which is immunized against a tumor antigen present in the tumor or a recipient subject having a cancer. Vaccination can for example be performed using a single neoAg, a single dose of vaccine, or the vaccine formulation to augment anti-tumor immunity. If no sufficient immunization is achieved, donors can be vaccinated with mRNA pentatope vaccines.

The term "subject" refers to any individual or patient to which the method described herein can be performed. Generally, the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

The terms "treat," "treating," "treatment," used interchangeably herein are meant to refer to reducing or ameliorating a disorder and/or symptoms associated therewith. It will be appreciated that, although not precluded, treating a disorder or condition does not require that the disorder, condition or symptoms associated therewith be completely eliminated.

The treatment described herein can be suitably administered to subjects, particularly humans, suffering from, having, susceptible to, or at risk for cancer or disease, disorder, or symptom thereof. Determination of those subjects "at risk" can be made by any objective or subjective determination by a diagnostic test or opinion of a subject or health care provider (e.g., genetic test, enzyme or protein marker, a marker (as defined herein), family history, and the like).

In one aspect, if the donor and recipient are ABO blood type incompatible and the peripheral blood cell composition comprises a number of red blood cells, then making the allogeneic lymphocyte composition further comprises reducing the number red blood cells. "ABO blood type incompatible," as used herein, refers to when the recipient has a major ABO red blood cell incompatibility against the donor, e.g., the recipient is blood type O and the donor is blood type A, B, or AB, the recipient is type A and the donor is type B or AB, or the recipient is type B and the donor is type A or AB.

In some aspects, the donor is a cancer-free donor, and wherein the cancer-free donor has at least one HLA Class II allele match to the subject having cancer.

As used herein, the term "donor" refers to the subject who is subjected to vaccination and from whom the cells are isolated to generate the lymphocyte composition. As further detailed throughout, the donor is an allogeneic donor, who is at least partially HLA-compatible with the recipient. By cancer-free, it is meant that the donor does not have a cancer, at least at the time a peripheral blood cell composition is obtained from the donor.

In some aspect, the number of red blood cells comprises less than or equal to about 50 ml in packed volume; e.g., less than or equal to about 50 ml in packed volume, preferably less than or equal to about 30 ml in packed volume, further "packed volume" should be defined, for example, centrifugation of the lymphocyte composition would result is a packed volume of 50 ml or less of red blood cells; a measured volume sample of the lymphocyte composition could also be screened to provide a proportionally representative volume of packed blood cells.

In some aspects, the antigen present in the recipient is selected from the group consisting of a neoplastic antigen, a neoplastic idiotype, a viral antigen, a bacterial antigen, a fungal antigen, a parasitic antigen, a non-human animal antigen, a tumor neoantigen, and a combination thereof.

"Tumor neoepitopes" or "tumor neoantigen" are epitopes identified by methods such as comparing the whole genome or whole exome sequence of tumor tissue versus the whole genome or whole exome sequence of non-tumor tissue from the same cancer patient, RNAseq to identify the expressed neoepitopes, and methods such as predictive algorithms, mono-allelic purification with tagged allele constructs, or deep motif deconvolution of immunopeptidomes to identify epitopes presented by specific HLA Class II alleles shared by the cancer patient and the cancer-free donor.

In various aspects, the antigen is a neoplastic antigen and wherein the neoplastic antigen is a tumor antigen.

In one aspect, the antigen present in the recipient is selected from the group consisting of a neoplastic antigen (neoplastic antigen is an antigen associated with a neoplasm where neoplasm is defined as any new and abnormal cellular growth, specifically one in which cellular replication is uncontrolled and progressive. Neoplasms may be benign, pre-malignant or malignant, and cancers are malignant neoplasms. Thus, all cancer antigens are neoplastic antigens but not all neoplastic antigens are cancer antigens. Neoplastic idiotype (Id) is a tumor-specific target, for example, in those B cell malignancies that express this molecule on their cell surface, for example, lymphoma or multiple myeloma, and include a viral antigen, a bacterial antigen, a fungal antigen, a parasitic antigen, and a non-human animal antigen.

In some aspects, the viral antigen is selected from the group consisting of a human papillomavirus (HPV) E6 antigen, a HPV E7 antigen and a combination thereof. In other aspects, the viral antigen is selected from the group consisting of an Epstein-Barr virus latent membrane protein 1 (LMP1), a latent membrane protein 2a (LMP 2a) and a combination thereof.

In one aspect, the tumor antigen is an antigen from a recipient's tumor.

In many aspects, a subject selected from the group consisting of the recipient, the donor and one or more potential allogeneic donor(s) has been screened for serological reactivity to an infectious agent antigen selected from the group consisting of a Human Immunodeficiency Virus (HIV) antigen, a Hepatitis Virus antigen, and a Cytomegalovirus antigen.

In some aspects, screening for one or more selection characteristic(s) is done and the screening is carried out on a subject selected from the group consisting the recipient, the donor, and one or more potential allogeneic donor(s). For example, a selection characteristic is screening for serological reactivity to an infectious agent antigen. An infectious agent antigen is selected from the group consisting of a Human Immunodeficiency Virus (HIV) antigen, a Hepatitis Virus antigen, and a Cytomegalovirus antigen. Important agents to be screened for include, for example, HIV-1 antigen(s), HIV-2 antigen(s), hepatitis A virus antigen(s), hepatitis B virus antigen(s), hepatitis C virus antigen(s), CMV antigens, infectious diseases, etc. If the virus or infectious agent or an antigen thereof were the target of the therapy, one would not rule out a donor having the desired CD4+ mediated immune response against that agent.

In one aspect, the infectious agent antigen is a Cytomegalovirus antigen, the recipient and the donor are screened, and there is no serological reactivity to the Cytomegalovirus antigen in the recipient or the donor. In one aspect, the viral antigen is an influenza antigen and the influenza antigen is a hemagglutinin antigen or a neuraminidase antigen.

In another aspect, a selection characteristic is screening for more than one HLA Class II alleles. In certain instances, a potential allogeneic donor is selected based on maximizing mismatch between the potential allogeneic donor versus the recipient, in the potential allogeneic donor versus recipient direction, at the more than one HLA Class II alleles, and the potential allogeneic donor is chosen as the donor. In certain instances, a selection characteristic is screening for one or more HLA Class I allele(s).

A potential allogeneic donor can be selected based on minimizing mismatch between the potential allogeneic donor and the recipient at the more than one HLA Class I allele(s), and the potential allogeneic donor is chosen as the donor.

In one aspect, the number of CD4+ T-cells in the allogeneic lymphocyte composition differs from the number of CD4+ T-cells in the peripheral blood cell composition by less than about 20%. In some embodiments, the CD4+ T-cells are less than about 50%, less than about 40%, preferably less than about 20%, more preferably less than about 10%. In some embodiments, ex vivo expansion of CD4+ T-cells may be performed, in such embodiments the number of CD4+ T-cells can greatly exceed the original number. Such expansion is an alternative embodiment. Further, "differs from the number of CD4+ T-cells in the peripheral blood cell composition by less than about 50%" means plus or minus less than 50% of the number of CD4+ T-cells in the peripheral blood cell composition. For example, if the number of CD4+ T-cells in the peripheral blood cell composition is $1 \times 10^5$ CD4+ cells, then "differs from the number of CD4+ T-cells in the peripheral blood cell composition by less than about 50%" means the number of CD4+ T-cells is between $1.5 \times 10^5$ and $0.5 \times 10^5$.

In various aspects, CD4+ T-cells obtained from the donor are not intentionally expanded or intentionally differentiated ex vivo. Intentionally expanded or intentionally differentiated is distinguished from expansion or differentiation of the CD4+ T-cells that is merely a side effect (not intentional, inadvertent) of the method, for example, CD4+ T-cells can sometimes undergo differentiation by coming into contact with plastic, other examples of such inadvertent events. In another embodiment, there is a further proviso that stem cells have not been mobilized in the peripheral blood cell composition donor who is allogeneic to the recipient.

In some aspects, reducing the CD8+ T-cells in the peripheral blood cell composition comprises using an anti-CD8+ antibody associated with magnetic particles or an anti-CD8+ antibody plus complement. The peripheral blood cell composition can be a whole blood product or an apheresis product, for example. Further, the HLA Class II allele mismatch in the donor versus the recipient direction can be a mismatch at HLA-DRB1. This limitation with an HLA Class II allele mismatch in the donor versus recipient direction is for example "graft-versus-host direction", wherein the at least one HLA Class II allele(s) mismatch in the direction of the allogeneic donor versus the recipient further comprises the same HLA Class II allele(s) mismatch between the allogeneic donor versus one or more first degree relatives of the recipient, which is desirable to preserve the opportunity for bone marrow transplantation from the first degree relatives to the recipient; ideally, all of the mismatches between donor versus recipient do not exist between a potential family bone marrow donor versus the recipient.

In one aspect, the number of donor CD4+ T-cells based on an ideal body weight of the recipient in kilograms (kg) is between about $1 \times 10^5$ CD4+ T-cells/kg and about $1 \times 10^9$ CD4+ T-cells/kg, In the composition, the number of donor CD4+ T-cells based on an ideal body weight (ideal body weight (IBW) is based on height. For men, IBW=50+2.3 kg/inch over 5 feet. For women, IBW=45.5+2.3 kg/inch over 5 feet) of the recipient in kilograms (kg) is between about $1 \times 10^5$ CD4+ T-cells/kg and about $1 \times 10^9$ CD4+ T-cells/kg (in a preferred embodiment, between about $1 \times 10^6$ CD4+ T-cells/kg and about $5 \times 10^8$ CD4+ T-cells/kg); the number of natural killer cells in the allogeneic lymphocyte composition is less than or equal to the number of natural killer cells in the peripheral blood cell composition, and the allogeneic lymphocyte composition has at least one order of magnitude fewer CD8+ T-cells relative to the peripheral blood cell composition.

In other aspects, the allogeneic lymphocyte composition has at least one order of magnitude fewer CD8+ T-cells relative to the peripheral blood cell composition.

In some aspects, the donor has CD4+ T-cell immunity against an antigen not present in the recipient.

In many aspects, donor has CD4+ T-cell immunity against the antigen present in the recipient. As used herein, "having CD4+ T-cell immunity" refers to the efficiency of the vaccination to induce an immune response in the donor, which translate into the expansion in the donor of new clones of CD4+ T-cells, directed against the specific antigen that was used for the vaccination purpose.

In other aspects, the recipient does not have detectable antibodies reactive against human leukocyte antigens of the donor.

In another embodiment, the invention provides a method of treating cancer in a subject including administering a lympho-depleting chemotherapy to the subject; and administering a lymphocyte composition to the subject, wherein the lymphocyte composition is obtained from a peripheral blood cell composition of an HLA-matched or—haploidentical donor vaccinated against a viral antigen and/or a tumor neoantigen present in the subject, wherein the composition is depleted of CD8+ T cells, and wherein the composition comprises an expanded population of CD4+ T cells specific to the viral and/or tumor neoantigen present in the subject.

The compositions and methods of the invention can be used against a broad range of cancers and tumor types, including but not limited to bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer. More particularly, cancers that may be treated by the compositions and methods described herein include, but are not limited to, the following: cardiac cancers, including, for example sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and limphoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis defoinians; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma. In certain embodiments, when the disease is cancer, it may include a lung cancer tumor, a breast cancer tumor, a prostate cancer tumor, a brain cancer tumor, or a skin cancer tumor for example.

Compositions of the invention may be administered to the individual by a variety of routes, for example, orally, topically, parenterally, intravaginally, systemically, intramuscularly, rectally or intravenously. In certain embodiments, the composition is formulated with a pharmaceutical carrier. Preferably, the composition is administered intravenously.

In some embodiments, the composition is combined with other anti-viral or anticancer therapies, such as administration of an anti-viral or anti-cancer agent, radiation therapy, phototherapy or immunotherapy. The anti-viral or anti-cancer agent can be administered with an invention composition either in the same formulation or in separate formulations, to enhance treatment. In these embodiments, the composition and the other therapies can be administered at the same time (simultaneously) or at separate times (sequentially), provided that they are administered in such a manner and sufficiently close in time to have the desired effect.

The compositions of the invention can also be administered in combination with existing methods of treating cancers, for example by chemotherapy, irradiation, or surgery. Thus, there is further provided a method of treating cancer comprising administering an effective amount of an invention composition to an individual in need of such treatment, wherein an effective amount of at least one further cancer chemotherapeutic agent is administered to the individual. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

In one aspect, making an allogeneic lymphocyte composition for administration to the subject comprises: vaccinating a human donor against an antigen present in a recipient, wherein the recipient is the subject; providing a peripheral blood cell composition from the human donor allogeneic to the recipient, the peripheral blood cell composition comprising a number of CD4+ T-cells, a number of CD8+ T-cells, and a number of natural killer cells, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, and (iii) the recipient does not have detectable antibodies reactive against human leukocyte antigens of the donor; and making the allogeneic lymphocyte composition from the peripheral blood cell composition by reducing the number of CD8+ T-cells in the peripheral blood cell composition by at least one order of magnitude, wherein the number of CD4+ T-cells in the allogeneic lymphocyte composition differs from the number of CD4+ T-cells in the peripheral blood cell composition by less than about 50%, and wherein the number of natural killer cells in the allogeneic lymphocyte composition is less than or equal to the number of natural killer cells in the peripheral blood cell composition.

In various aspects, prior to administering to the subject the allogeneic lymphocyte composition the method further comprises administering a lympho-reductive non-lympho-ablative treatment to the subject to induce transient lymphopenia in the subject; administering a treatment to deplete or inhibit myeloid-derived suppressor cells; administering a treatment to deplete or inhibit tumor associated macrophage cells or administering a treatment to deplete regulatory T cells; or wherein subsequent to administering to the subject the allogeneic lymphocyte composition the method further comprises administering a drug to induce selective depletion of alloreactive T-cells.

In one aspect, the lympho-reductive non-lympho-ablative treatment comprises treating the subject with one or more cyto-reductive agent selected from the group consisting of alkylating agents, alkyl sulphonates, nitrosoureas, triazenes, antimetabolites, pyrimidine analogs, purine analogs, *vinca* alkaloids, epipodophyllotoxins, antibiotics, dibromomannitol, deoxyspergualine, dimethyl myleran and thiotepa. In one aspect, the lymphoreductive non-lymphoablative treatment comprises treating the subject with an alkylating agent and the alkylating agent is cyclophosphamide. In one aspect, subsequent to administering the first allogeneic lymphocyte composition to the subject, the method further comprises administration of an anti-tumor monoclonal antibody or anti-tumor monoclonal antibody/drug conjugate to the subject.

A "lympho-depleting therapy", "lympho-reductive therapy", and the like are meant to refer to drugs or other agents, such as chemotherapies, that reduce the concentration of lymphocytes in the peripheral blood. By "reduce", it is meant a negative alteration of at least 10%, 25%, 50%, 75%, or 100%.

In one aspect, method further comprises administration of the anti-tumor monoclonal antibody and the anti-tumor monoclonal antibody is selected from the group consisting of rituximab, cetuximab, trastuzumab, and pertuzumab. In one aspect, the invention comprises administration of the anti-tumor monoclonal antibody/drug conjugate and the anti-tumor monoclonal antibody/drug conjugate is selected from the group consisting of brentuximab vedotin, gemtuzumab ozogamicin, trastuzumab emtansine, inotuzumab ozogamicin, glembatumumab vedotin, lorvotuzumab mertansine, cantuzumab mertansine, and milatuzumab-doxorubicin. In some aspects, admistration is first the allogeneic lymphocyte composition and then administration of a chemotherapeutic agent to the subject. For example, the chemotherapeutic agent is selected from the group consisting of dasatinib, nilotinib, ponatinib, imatinib, lapatinib, and vismodegib.

In other aspects, prior to administering to the subject the allogeneic lymphocyte composition the treatment comprises administration of a drug selected from the group consisting of dasatinib, 5-fluorouracil, taxotere, clodronate, gemcitabine, cyclophosphamide, fludarabine, denileukin diftitox, and daclizumab.

In some aspects, the peripheral blood cell composition is a whole blood product or an apheresis product.

In various aspects, the subject has been injected with a nanoparticle composition into a tumor, wherein the nanoparticle composition comprises nanoparticles comprising an antigen not present in the subject. In many aspects, the nanoparticles further comprise a cytokine, wherein the cytokine is an interleukin and is selected from the group consisting of IL-2, IL-7, IL-12, and IL-15; or the cytokine is an interferon and is selected from the group consisting of interferon gamma, interferon beta, interferon alpha, interferon, tau, interferon omega, and consensus interferon.

In an additional embodiment, the invention provides a cell bank including CD4+ T cells specific for a viral antigen, a tumor neoantigen, or a combination thereof, wherein the cell bank includes CD4+ T cells from collected from donors of different human leukocyte antigen (HLA) types.

In various aspects, the viral antigen is an HPV antigen.

In one embodiment, the invention provides an allogeneic lymphocyte composition for administration to a human recipient obtained by the method of the invention as described herein.

If the recipient is seropositive for the CMV antigen, then the status of the donor does not matter. In certain embodiments wherein the donor is not immunized to an antigen that is present in, or will be delivered to, the recipient, the delivery of CD4+ T-cell help is contingent upon donor CD4+ T-cell recognition of allogeneic HLA Class II molecules on the recipient's cells. An example of an "ideal donor" for the purpose of exemplifying these embodiments of the present invention is then completely mismatched at HLA Class II alleles (in particular, HLA-DRB1, HLA-DQB1, and HLA-DPB1) and completely matched for Class I alleles (to maximize survival of donor cells in the recipient and minimize alloantibody formation against Class I molecules). Further, the ideal donor is completely mismatched with unshared HLAs of first-degree relatives of the recipient who are potential donors for allogeneic stem cell transplantation.

In one embodiment, there is an allogeneic lymphocyte composition derived from a peripheral blood cell composition of a human, allogeneic donor for administration to a human recipient, the allogeneic lymphocyte composition comprising a number of CD4+ T-cells and a number of natural killer cells from the peripheral blood cell composition of the donor, wherein (i) the donor comprises at least one human leukocyte antigen (HLA) Class II allele mismatch relative to the recipient in the donor versus the recipient direction and the HLA Class II allele mismatch is at a gene selected from the group consisting of HLA-DRB1, HLA-DQB1, and HLA-DPB1, (ii) the recipient does not have detectable antibodies reactive against human leukocyte antigens of the donor, (iii) the number of CD4+ T-cells in the allogeneic lymphocyte composition differs from the number of CD4+ T-cells in the peripheral blood cell composition by less than about 50%. (including but not limited to less than about 50%, less than about 40%, preferably less than about 20%, more preferably less than about 10%).

Also provided is a method of treating a disease or condition in a human subject, comprising administering a lympho-reductive (in some embodiments of this aspect of the present invention, it is desirable to provide a lympho-reductive non-lympho-ablative treatment to promote the homeostatic expansion and differentiation of the administered lymphocyte composition; in other embodiments it is desirable that the treatment also be myelo-reductive (i.e., inhibiting or depleting suppressive myeloid populations including myeloid-derived suppressor cells, tumor associate macrophage, and or N2 neutrophils) non-lympho-ablative treatment to the subject to induce transient lymphopenia in the subject; and subsequently administering to the subject a first allogeneic lymphocyte composition derived from a peripheral blood cell composition of a human, allogeneic donor, the first allogeneic lymphocyte composition comprising a number of CD4+ T-cells and a number of natural killer cells from the peripheral blood cell composition of the donor, wherein (i) the donor comprises at least one human leukocyte antigen (HLA) Class II allele mismatch relative to the subject in the donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the donor, (iii) the number of CD4+ T-cells in the first allogeneic lymphocyte composition differs from the number of CD4+ T-cells in the peripheral blood cell composition by less than about 50%, (iv) the number of donor CD4+ T-cells based on an ideal body weight of the subject in kilograms (kg) is between about $1 \times 10^5$ CD4+ T-cells/kg and about $1 \times 10^9$ CD4+ T-cells/kg, (v) the number of natural killer cells in the first allogeneic lymphocyte composition is less than or equal to the number of natural killer cells in the peripheral blood cell composition, and (vi) the first allogeneic lymphocyte composition has at least one order of magnitude fewer CD8+ T-cells relative to the peripheral blood cell composition.

While not wishing to be bound by a particular theory, the infused CD4+ cells provide signals to other cell types, predominately the subject's CD8+, macrophage, and/or antigen presenting cells that augment cytotoxic function of these cells in the subject (tolerized CD4+ of subject/exhausted CD8+ of subject); an example of treatment of a disease or condition by this method should be exemplified, at least treatment of myelodysplastic syndrome.

In one aspect, kits are provided for use in treating a disease or condition in a subject, the kit comprising: a lymphocyte composition as described herein wherein the subject is the human recipient; and a nanoparticle composition comprising nanoparticles comprising the antigen not present in the human recipient. In one aspect, the nanoparticles further comprise a cytokine, for example, an interleukin or an interferon. The cytokine can be an interleukin and is selected from the group consisting of IL-2, IL-7, IL-12, and IL-15. The cytokine is may be an interferon e.g., interferon gamma, interferon beta, interferon alpha, interferon, tau, interferon omega, and consensus interferon.

The nanoparticles may further comprise a compound selected from the group consisting of a chemokine, an imaging agent, a photo antenna molecule, a thermal antenna molecule, and a Toll-like receptor ligand, ligands that promote differentiation of CD4+ T-cells into Type I (e.g., IFN-gamma producing) CD4+ memory T-cells, ligands for receptors that induce activation of antigen presenting cells (e.g., anti-CD40 antibodies or aptamers). Further, the nanoparticles may include an agent that targets the nanoparticles to tumor cells or antigen-presenting cells.

In one aspect, subsequent to administering the first allogeneic lymphocyte composition to the subject, the method further comprises administration of a monoclonal antibody/CD4+ T-cell epitope conjugate to the subject. In one aspect, subsequent to administering the first allogeneic lymphocyte composition to the subject, the method further comprises administering a successive lympho-reductive non-lympho-ablative treatment to the subject to induce transient lymphopenia in the subject; and subsequently administering to the subject a successive allogeneic lymphocyte composition derived from an additional peripheral blood cell composition of an additional human, allogeneic donor, the successive allogeneic lymphocyte composition comprising a number of CD4+ T-cells and a number of natural killer cells from the additional peripheral blood cell composition of the additional donor, wherein (i) the additional donor comprises at least one human leukocyte antigen (HLA) Class II allele mismatch relative to the subject in the additional donor versus the subject direction and the HLA Class II allele mismatch is at a gene selected from the group consisting of HLA-DRB1, HLA-DQB1, and HLA-DPB1, (ii) the subject does not have detectable antibodies reactive against human leukocyte antigens of the additional donor, (iii) the number of CD4+ T-cells in the successive allogeneic lymphocyte composition differs from the number of CD4+ T-cells in the additional peripheral blood cell composition by less than about 50%, (iv) the number of additional donor CD4+ T-cells based on an ideal body weight of the subject in kilograms (kg) is between about $1 \times 10^5$ CD4+ T-cells/kg and about $1 \times 10^9$ CD4+ T-cells/kg, (v) the number of natural killer cells in the successive allogeneic lymphocyte composition is less than or equal to the number of natural killer cells in the additional peripheral blood cell composition, and (vi) the successive allogeneic lymphocyte composition has at least one order of magnitude fewer CD8+ T-cells relative to the additional peripheral blood cell composition. Subsequent to administering the first allogeneic lymphocyte composition to the subject, the method further comprises administration of an agent that blocks negative signaling in T-cells. The agent that blocks negative signaling in T-cell is selected from the group consisting of an anti-PD-1 antibody, ipilimumab, an anti-PD-L2 antibody, and a PD-1 fusion protein. The disease or condition is selected from the group consisting of a cancer, an autoimmune disorder, an organ transplantation, an allograft rejection, and a viral infection. For example, the disease or condition is a cancer and the cancer is myelodysplastic syndrome.

In one embodiment, the invention provides a method of making an allogeneic lymphocyte composition for administration to a human recipient, comprising providing a peripheral blood cell composition from a human donor allogeneic to the recipient, the peripheral blood cell composition comprising a number of CD4+ T-cells, a number of CD8+ T-cells, and a number of natural killer cells, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, and (iii) the recipient does not have detectable antibodies reactive against human leukocyte antigens of the donor; and making the allogeneic lymphocyte composition from the peripheral blood cell composition by reducing the number of CD8+ T-cells in the peripheral blood cell composition by at least one order of magnitude, wherein (a) the number of CD4+ T-cells in the allogeneic lymphocyte composition differs from the number of CD4+ T-cells in the peripheral blood cell composition by less than about 50%, and (b) the number of natural killer cells in the allogeneic lymphocyte composition is less than or equal to the number of natural killer cells in the peripheral blood cell composition.

In one aspect, a potential allogeneic donor is selected from the one or more potential allogeneic donor(s) based on minimizing mismatch between the potential allogeneic donor and the recipient at the more than one HLA Class II alleles, and the potential allogeneic donor is chosen as the donor. A potential allogeneic donor is selected from the one or more potential allogeneic donor(s) based on minimizing mismatch between the potential allogeneic donor and the recipient at the one or more HLA Class I allele(s), and the potential allogeneic donor is chosen as the donor.

In one aspect, the antigen present in the recipient against which the donor has immunity is a viral antigen and the viral antigen is selected from the group consisting of a human papillomavirus antigen, an Epstein Barr Virus antigen, a Kaposi's sarcoma-associated herpesvirus (KSHV) antigen, a Hepatitis A virus antigen, a Hepatitis B virus antigen, and a Hepatitis C virus antigen. For example, the viral antigen is a human papillomavirus antigen and the human papillomavirus antigen is an E6 or an E7 antigenic peptide. In one aspect, the number of CD4+ T-cells in the allogeneic lymphocyte composition differs from the number of CD4+ T-cells in the peripheral blood cell composition by less than about 20%.

In one embodiment is provided an allogeneic lymphocyte composition derived from a peripheral blood cell composition of a human, allogeneic donor for administration to a human recipient, the allogeneic lymphocyte composition comprising a number of CD4+ T-cells and a number of natural killer cells from the peripheral blood cell composition of the donor, wherein (i) the donor has CD4+ T-cell immunity against an antigen present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, (iv) the number of CD4+ T-cells in the allogeneic lymphocyte composition differs from the number of CD4+ T-cells in the peripheral blood cell composition by less than about 50%, the number of donor CD4+ T-cells based on an ideal body weight of the recipient in kilograms (kg) is between about $1 \times 10^5$ CD4+ T-cells/kg and about $1 \times 10^9$ CD4+ T-cells/kg, the number of natural killer cells in the allogeneic lymphocyte composition is less than or equal to the number of natural killer cells in the peripheral blood cell composition, and the allogeneic lymphocyte composition has at least one order of magnitude fewer CD8+ T-cells relative to the peripheral blood cell composition.

The invention provides an allogeneic lymphocyte composition derived from a peripheral blood cell composition of a human, allogeneic donor for administration to a human recipient, the allogeneic lymphocyte composition comprising a number of CD4+ T-cells and a number of natural killer cells from the peripheral blood cell composition of the donor, wherein (i) the donor has CD4+ T-cell immunity against an antigen not present in the recipient, (ii) the donor comprises at least one human leukocyte antigen (HLA) Class II allele match relative to the recipient and the HLA Class II allele match is at a gene selected from the group consisting of HLA-DRB1, HLA-DQB1, and HLA-DPB1, (iii) the recipient does not have detectable antibodies reactive against human leukocyte antigens of the donor, the number of CD4+ T-cells in the allogeneic lymphocyte composition differs from the number of CD4+ T-cells in the peripheral blood cell composition by less than about 50%, the number of donor CD4+ T-cells based on an ideal body weight of the recipient in kilograms (kg) is between about $1 \times 10^5$ CD4+ T-cells/kg and about $1 \times 10^9$ CD4+ T-cells/kg, (vi) the number of natural killer cells in the allogeneic lymphocyte composition is less than or equal to the number of natural killer cells in the peripheral blood cell composition, and (vii) the allogeneic lymphocyte composition has at least one order of magnitude fewer CD8+ T-cells relative to the peripheral blood cell composition.

The invention provides a method of treating a disease or condition in a human subject, comprising administering to the subject an allogeneic lymphocyte composition derived from a peripheral blood cell composition of a human, allogeneic donor, the allogeneic lymphocyte composition comprising a number of CD4+ T-cells and a number of natural killer cells from the peripheral blood cell composition of the donor, wherein (i) the donor has CD4+ T-cell immunity against an antigen present in the subject, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogeneic lymphocyte composition differs from the number of CD4+ T-cells in the peripheral blood cell composition by less than about 50%, (v) the number of donor CD4+ T-cells based on an ideal body weight of the subject in kilograms (kg) is between about $1 \times 10^5$ CD4+ T-cells/kg and about $1 \times 10^9$ CD4+ T-cells/kg, (vi) the number of natural killer cells in the allogeneic lymphocyte composition is less than or equal to the number of natural killer cells in the peripheral blood cell composition, and (vii) the allogeneic lymphocyte composition has at least one order of magnitude fewer CD8+ T-cells relative to the peripheral blood cell composition.

In methods of the invention described herein, optionally before administering to the subject the allogeneic lymphocyte composition the method further comprises administering a treatment to deplete or inhibit myeloid-derived suppressor cells. The treatment to deplete or inhibit myeloid-derived suppressor cells may comprise administration of a drug selected from the group consisting of dasatinib, 5-fluorouracil, taxotere, clodronate, and gemcitabine for example. Optionally, before administering to the subject the allogeneic lymphocyte composition the method further comprises administering a treatment to deplete or inhibit tumor associated macrophage cells. Optionally, before administering to the subject the allogeneic lymphocyte composition the method further comprises administering a treatment to deplete regulatory T cells. The treatment to deplete regulatory T cells may include administration of a drug selected from the group consisting of cyclophosphamide, idelalisib, denileukin diftitox, and daclizumab.

In another embodiment, the invention provides a method of treating a disease or condition in a human subject comprising injecting a nanoparticle composition into a tumor (nanoparticles can be injected into or infused into the subject, wherein the nanoparticles further comprise a targeting agent, and the targeting agent binds to a target cell such as a dispersed/non-localized neoplasm (e.g., a lymphoma or leukemia) where direct injection to all possible sites is not practical or feasible), wherein the nanoparticle composition comprises nanoparticles comprising an antigen not present in the subject, thus introducing the antigen into the subject; administering to the subject an allogeneic lymphocyte composition derived from a peripheral blood cell composition of a human, allogeneic donor, the allogeneic lymphocyte composition comprising a number of CD4+ T-cells and a number of natural killer cells from the peripheral blood cell composition of the donor, wherein (i) the donor has CD4+ T-cell immunity against the antigen, (ii) the donor comprises at least one human leukocyte antigen (HLA) Class II allele match relative to the subject and the HLA Class II allele match is at a gene selected from the group consisting of HLA-DRB1, HLA-DQB1, and HLA-DPB1, (iii) the subject does not have detectable antibodies reactive against human leukocyte antigens of the donor, (iv) the number of CD4+ T-cells in the allogeneic lymphocyte composition differs from the number of CD4+ T-cells in the peripheral blood cell composition by less than about 50%, (v) the number of donor CD4+ T-cells based on an ideal body weight of the subject in kilograms (kg) is between about $1\times10^5$ CD4+ T-cells/kg and about $1\times10^9$ CD4+ T-cells/kg, (vi) the number of natural killer cells in the allogeneic lymphocyte composition is less than or equal to the number of natural killer cells in the peripheral blood cell composition, and (vii) the allogeneic lymphocyte composition has at least one order of magnitude fewer CD8+ T-cells relative to the peripheral blood cell composition. In one aspect, the antigen is a nonhuman animal antigen and the non-human animal antigen is a keyhole limpet hemocyanin antigen. In another aspect, the antigen is a viral antigen and the viral antigen is selected from the group consisting of a human papillomavirus antigen, an Epstein Barr Virus antigen, a Kaposi's sarcoma-associated herpesvirus (KSHV) antigen, a Hepatitis A virus antigen, a Hepatitis B virus antigen, and a Hepatitis C virus antigen.

The following examples are intended to illustrate but not limit the invention.

EXAMPLES

The myelodysplastic syndromes (MDS) are a diverse group of malignant stem cell disorders characterized by dysplastic and ineffective bone marrow production of blood cells and a variable risk of transformation to acute leukemia. These disorders may develop de novo or arise years after exposure to potentially mutagenic chemotherapy.

Approximately 12,000-20,000 new cases of MDS will be diagnosed in the United States this year with a median age of onset of between 60 and 72. Current treatment outcomes for the myelodysplastic syndromes have been disappointing. Age, performance status, and disease risk category, as determined by the International Prognostic Scoring System (IPSS), usually determine the choice of treatment modality. Patients <60 years of age, who have good or excellent performance status and who are in the IPSS intermediate-2 or high risk categories, would predominantly be considered for high intensity therapies, since these IPSS categories confer a median survival of 1.2 and 0.4 years, respectively. High-intensity therapies are defined as treatments requiring hospitalization, including intensive combination chemotherapy and hematopoietic cell transplantation.

Patients in the low or intermediate-1 category would generally be considered for low intensity therapies. These include treatments that can be administered in the outpatient clinic, such as hematopoietic growth factors, differentiation-inducing agents, biologic response modifiers, and low intensity chemotherapy. Patients with poor performance status would be considered for supportive care or low intensity therapies.

Example 1—IDE Device

The investigational agent to be used in this trial is the CliniMACS system with CliniMACS® CD8 reagent, a medical device that is used to enrich or deplete CD8+ T cells from human blood products. The CliniMACS® System intended for selection of CD8+ cells comprises four primary components: 1) CliniMACS® CD8 Reagent—colloidal super paramagnetic iron-dextran beads linked to a murine antibody against human CD8; 2) CliniMACSplus Instrument—a software controlled instrument that processes the blood sample (cell product); 3) CliniMACS® Tubing Set, (Standard or LS)—a single-use, sterile, disposable tubing set with two proprietary cell selection columns; and 4) CliniMACS® PBS/EDTA Buffer—a sterile, isotonic phosphate buffered, 1 mM EDTA, saline solution, used as external wash and transport fluid for the in vitro preparation of blood cells. The system utilizes magnetic cell sorting (MACS®), a powerful tool for the isolation of many cell types, to selectively enrich or deplete the cell population of interest. In this case, CD8+ T cells are labeled with a monoclonal antibody linked to super-paramagnetic particles and then are depleted from the blood product by passage through the CliniMACS system, which incorporates a strong permanent magnet and a separation column with a ferromagnetic matrix to remove the labeled cells. The therapeutic agent, CD8+ T cell-depleted blood cells, comes out of the device and is not intended to contain any component of the device.

Example 2—Transiently Engrafting Donor Lymphocytes Induce Clinical Tumor Responses To date, only two therapies are capable of prolonging the survival of patients with MDS. The first, allogeneic BMT, has achieved some long term cures, as well as delay in disease progression. This therapy is only applicable to a small fraction of affected patients due to age, donor availability, and comorbidities. The second is the methyltransferase inhibitor, 5-azacitidine. This therapy has been shown to prolong median survival by 7 months compared to supportive care alone. Some patients with MDS respond to immunosuppressive regimens, such as cyclosporine, antithymocyte globulin (ATG) or steroids, with a sustained increase in blood counts. This finding is similar to aplastic anemia, where immunosuppression treats the autoimmune component leading to the cytopenias. The favorable results obtained with agents that specifically target the immune system suggest that MDS is a disease that is susceptible to immune modulation. One potential explanation for the benefit of ATG, cyclosporine, and steroids is that these drugs unmask the activity of an endogenous anti-tumor immune response by selectively inhibiting or killing lymphocytes that suppress anti-tumor immunity. Further, potential evidence for the existence of a cryptic, endogenous immune response against MDS was seen in a trial of non-myeloablative, partially HLA-mismatched (haploidentical) allogeneic bone marrow transplantation, in which five patients experienced disease responses despite graft rejection. All five patients had at least transient reductions in the percentage of bone marrow blasts, and three of five patients, each of whom was dependent upon red blood cell +/−platelet transfusions prior to transplantation, became transfusion independent. Table 1 demonstrates that, despite absence of donor cell engraftment on day 30 after BMT, at least three of five patients had a reduction of marrow blasts lasting at least six months after BMT.

TABLE 1

| Patient # (age in years) | Diagnosis | Donor chimerism (Day 30) | Blast % Pre- BMT | Blast % Post BMT (day) |
| --- | --- | --- | --- | --- |
| 1 (39) | RAEB-t | 0 | 22 | 0 (181+) |
| 2 (62) | AA → RAEB | 0 | 15 | 0 (378) |
| 3 (62) | PCV → RAEB | 0 | 8 | 0 (342) |
| 4 (56) | RAEB | 0 | 5 | 2 |
| 5 (59) | RAEB-t | 0 | 20 | 4 (73) 50 (78) |

FIG. 1 shows the hematocrits of the same five patients after BMT, with the jagged portions reflecting the effect of transfusion. Three of five patients became transfusion independent, with patient #1 remaining in morphologic and hematologic remission for at least three years. More interestingly, patient #2 demonstrated a delayed hematologic response, becoming transfusion independent four months after BMT and three months after documentation of graft rejection. In light of the sensitivity of MDS to immunotherapy, the possibility that an endogenous (i.e. host-derived) anti-tumor immune response can be reawakened by the immunological perturbation provided by the transiently engrafting donor lymphocytes was raised. This postulated mechanism, the awakening of an endogenous anti-response following graft rejection, may also account for the induction of leukemia remission in patients receiving white blood cell transfusions after either no conditioning or only 100 cGy total body irradiation. The hypothesis that transiently engrafting donor lymphocyte infusions (DLI) can induce antitumor immune responses from host T cells in a mouse model was tested. BALB/c×C57BL/6 $F_1$ mice were treated with Cy on day −1, and on day 0 they received $10^6$ A20 lymphoma cells (of BALB/c origin) IV together with nothing, haploidentical DLI alone, autologous tumor cell vaccine alone, or DLI+vaccine. Compared to animals receiving either no treatment or vaccine alone after Cy conditioning, those that were conditioned with Cy and then treated with DLI alone or DLI+vaccine survived significantly longer, with apparent cure achieved in five and four animals, respectively (FIG. 2). None of the nine cured animals had any detectable donor chimerism when tested >100 days after DLI, suggesting that the donor T cells were rejected.

Figure 3B:
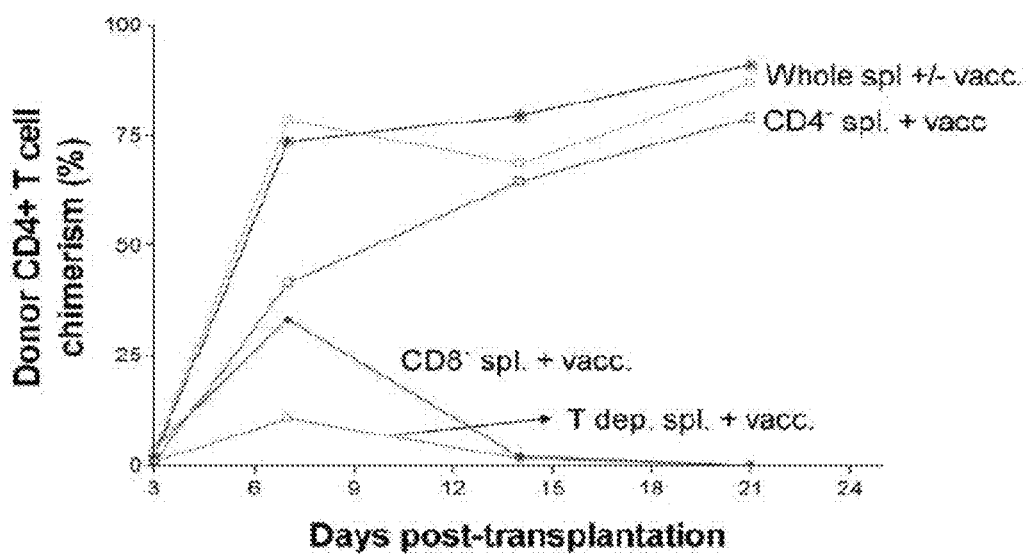
FIG. 3B shows a graph with donor CD4+ T cell chimerism and days post-transplantation.

These results demonstrated that the combination of Cy followed by partially MHC-mismatched DLI induced significant anti-tumor effects. In order to characterize the role of donor CD4+ versus CD8+ T cells in the antitumor effect, the experiment was repeated in recipients of Cy+vaccine+50 million mismatched spleen cells that were either untreated or depleted of CD4+ T cells, CD8+ T cells, or both. In this experiment, recipients of whole spleen DLI all died of GVHD before day 20 (FIG. 3A). In contrast, mice that received vaccine plus CD8+ T cell depleted spleen cells lived significantly longer than mice receiving vaccine plus pan-T cell depleted spleen cells (p=0.04), indicating that depletion of CD8+ T cells abrogated lethal GVHD without abrogating anti-tumor immunity. In order to understand why depletion of CD8+ T cells from the allogeneic DLI abrogated GVHD, the survival of donor cells in mice conditioned with Cy and then infused with mismatched spleen cells, either untreated or depleted of either or both T cell subsets was studied. Interestingly, CD8+ T cell-depleted spleen cells engrafted only transiently, with donor CD4+ T cell chimerism peaking at 7 days after DLI and declining to undetectable levels by day 21 (FIG. 3B). In contrast, sustained engraftment of donor cells was seen in all mice receiving DLI containing CD8+ T cells, and most of these animals eventually died of GVHD. Taken together, the animal studies demonstrate that Cy followed by CD8+ T cell depleted DLI induces transient engraftment of donor cells and significant anti-tumor effects without inducing acute GVHD. More recently, it was found that depletion of host CD8+ T cells prior to "Cy+DLI" significantly diminishes the therapeutic effect, strongly implicating host CD8+ T cells as critical mediators of the anti-tumor effect.

Example 3—Clinical Experience with CD8+ T Cell Depleted Allogeneic Stem Cell or Lymphocyte Infusions There are no reports of patients treated with Cy followed by an infusion of CD8+ T cell depleted PBCs from haploidentical donors, so it is not possible to provide preliminary safety data. However, there have been reports of patients undergoing alloBMT who have received CD8+ T cell-depleted grafts or of patients in relapse after alloBMT who have received CD8+ T cell depleted PBMC infusions. The goal of CD8+ T cell depletion was to reduce the incidence of GVHD while preserving the anti-leukemia effect of the infusion. With regard to GVHD, the studies did not yield a conclusive answer, with some showing a possible benefit and others showing none. Interestingly, infusion of CD8+ T cell-depleted DLI induced the activation of endogenous CD8+ T cells, a finding that is consistent with the hypothesis that CD8+ T cell-depleted DLI can effectively awaken a host CD8+ T cell response against cancer.

The results of two other studies are germane to considerations of the safety of the proposed clinical trial. In the first study, patients with various hematologic malignancies received marrow from unrelated donors that were mismatched for either one HLA-DR allele or one HLA Class I (HLA-A or HLA-B) antigen. Patients received CD4+ T cell depleted grafts containing titrated doses of CD8+ T cells. The major finding was that graft rejection occurred despite myelo-ablative conditioning in six of ten patients receiving grafts containing <3.1×10$^6$ CD8+ T cells/kg of recipient body weight but in none of fifteen patients receiving >3.1×10$^6$ CD8+ T cells/kg. Thus, even after myelo-ablative condoses that are well below the threshold for engraftment or GVHD induction. In comparison, the five patients who responded despite graft rejection received marrows containing a median of 1.43×10$^7$ CD4+ T cells/kg (range 0.84-3.14×10$^7$/kg) and 1.86×10$^7$ CD8+ T cells/kg (range 0.43-2.16×10$^7$/kg). Therefore, MDS patients are capable of rejecting haploidentical cell infusions containing this many T cells.

TABLE 2

CE8 Depleted Cell Product Validation Results

| | % CD4+ Cells | Total CD4+ Cells | % CD8+ Cells | Total CD8+ Cells | CD8+ Cells Log Depletion | Percent Viable | Sterility Result |
|---|---|---|---|---|---|---|---|
| Depletion #1 | 39.6% | 7.6 × 10$^8$ | 0.5% | 9.5 × 10$^6$ | 1.95 | 98% | Negative |
| #2 | 11.6% | 2.5 × 10$^8$ | 0.03% | 6.5 × 10$^5$ | 2.43 | 90% | Negative |
| #3 | 39.9% | 3.0 × 10$^8$ | 0.03% | 2.3 × 10$^5$ | 2.67 | 97% | Negative | ditioning, CD8+ T cell depletion significantly increases the risk of graft rejection, which nullifies the risk of graft-induced aplasia and GVHD.

In the second study patients received T cell-depleted, haploidentical peripheral blood stem cell (PBSC; n=15) or PBSC plus marrow grafts (n=28) containing a mean of 2.7×10$^4$ or 3.5×10$^4$ CD3+ T cells/kg, respectively, which translates to CD8+ T cell doses of approximately 1-1.5×10$^4$/kg. To facilitate engraftment in the face of T cell depletion, patients were conditioned intensively and received "mega-dose" stem cell grafts containing a mean of 14.0×10$^6$ or 10.6×10$^6$ CD34+ cells/kg for recipients of PBSC only versus PBSC plus marrow, respectively. In light of the low T cell content, no GVHD prophylaxis was administered. Engraftment occurred in all 43 patients, and no patient experienced acute or chronic GVHD as a result of the transplantation procedure. These data demonstrate that even when sustained engraftment occurs in patients receiving myelo-ablative conditioning, haploidentical grafts containing <10$^4$ CD8+ T cells/kg are unlikely to cause GVHD. Since the device usually achieves >2 log depletion of CD8+ T cells, the starting dose of CD8+ T cell depleted PBCs on the trial will likely contain fewer than 10$^4$ CD8+ T cells/kg. It is likely, then, that no patients receiving this dose will engraft or experience GVHD, even if sustained engraftment occurs.

Example 4—CD8 Depletion Using the CliniMACS System with CliniMACS-CD8 Reagent

Figure 4:
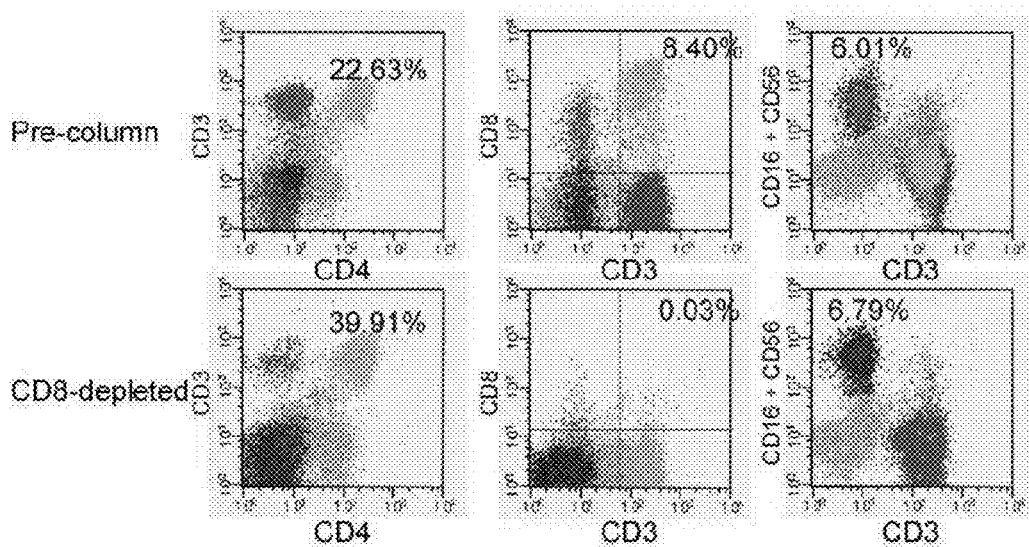
FIG. 4 shows validation runs for CD8 depletion using leukapheresis product and phlebotomy specimens (flow cytometry results).

For this trial, CD8+ T cells will be depleted using the CliniMACS_system with the CliniMACS_CD8 Reagent (Miltenyi Biotec, Woburn, MA). Three validation runs were performed, the first using a leukapheresis product, and the last two using phlebotomy specimens. Flow cytometry results from the last depletion are shown in FIG. 4, demonstrating excellent depletion of CD8+ T cells, from 8.40% to 0.03% of total cells, and a corresponding enrichment of CD4+ T cells and CD16+ or CD56+ NK cells. The table below demonstrates all three products meet the protocol criterion of having a CD8+ T cell number that is <3.2% of the CD4+ T cell number. Had products #2 and #3 been used to deliver a dose of 10$^6$ CD4+ T cells/kg to a recipient with an ideal body weight of 70 kg, they would have contained 2.6×10$^3$ and 7.7×10$^2$ CD8+ T cells/kg IBW, respectively, Example 5—Correlative Laboratory Studies to Predict Response to Therapy In light of the potential toxicities of immunosuppressive therapies, such as antithymocyte globulin, in patients with MDS, numerous investigators have endeavored to identify patient characteristics that correlate with response to therapy. Such characteristics that predict disease response include hypocellular marrow, abnormal T cell receptor repertoire by T cell receptor beta chain variable region CDR3 size by spectratype analysis, presence of cells with a phenotype characteristic of paroxysmal nocturnal hemoglobinuria (PNH), expression of HLADR15, trisomy 8, younger age, and shorter transfusion history. One goal was thus to determine whether characteristics that predict response to immunosuppressive therapy can also predict response to Cy+CD8+ T cell-depleted haploidentical DLI. Patients entered onto this trial will have examination of T cell receptor beta chain variable region diversity both before and after therapy. Cytogenetics and HLA typing will be performed routinely on all patients.

Recent studies have uncovered a role for donor natural killer cell alloreactivity in preventing relapse of acute leukemia after haploidentical stem cell transplantation. More recently, alloreactive natural killer cells of donor origin have been found to prevent relapse of AML and MDS after HLA-identical stem cell transplantation. These results underscore the need to characterize the expressed repertoire of killer immunoglobulin-like receptors, or KIRs, on donor NK cells using both molecular and flow cytometric methods so as to identify donors expressing KIRs whose HLA ligands are missing on recipient cells.

Example 6—Rationale for the Proposed Trial Design

This is a standard phase I/II trial design that seeks to determine, in the phase I portion of the trial, the maximally tolerated dose (MTD) of CD8+ T cell-depleted haploidentical peripheral blood cells (CD8– PBCs) when infused after cyclophosphamide (Cy), and then to estimate, in the phase II portion of the trial, the efficacy of treatment with Cy plus the MTD of CD8– PBCs. High dose Cy (>100 mg/kg) has been used extensively as part of transplantation conditioning for patients with hematologic malignancies, and its safety is well-documented in this population, including elderly patients (ages 55-66) with myelodysplastic syndrome. The most serious risks of treatment, because they have the potential to cause death, are prolonged aplasia and graft-versus host disease, both of which require sustained engraftment of the donor cells. The choice of the initial cell dose, $10^5$ CD4+ T cells/kg and $<3.2\times10^3$ CD8+ T cells/kg, was based solely upon safety considerations. Specifically, grafts containing $<10^4$ CD8+ T cells/kg do not cause severe GVHD, even among patients receiving lethal conditioning and no pharmacologic immunosuppression after transplantation. Moreover, partial depletion of CD8+ T cells from standard marrow grafts significantly increases the risk of graft rejection33, which is the desired outcome of treatment in this trial. For these reasons, it is felt that a DLI product containing $<10^4$ CD8+ T cells/kg is unlikely to cause serious adverse events.

Experience with haploidentical DLI, without CD8+ T-cell depletion, has been recently published. In a phase I/II trial, 41 patients with relapsed/refractory malignancies received non-ablative conditioning with 100 cGy total body irradiation, followed by infusion of $1\times10^6$ to $2\times10^8$ haploidentical CD3+ cells/kg, with 29 patients receiving the highest dose. Objective responses were achieved at the higher dose levels. Notably, $1\times10^8$ CD3+ cells/dose was the minimum dose associated with response (25% response rate, or 2 of 8 patients), with $2\times10^8$ CD3+ cells/dose (the highest evaluated) associated with the greatest response rate (nearly 50%, in 10 of 21 patients). As proof of principle, all responses occurred in the absence of sustained donor chimerism. In the highest dose cohort, transient donor chimerism was seen but disappeared by 2 weeks in most patients, with one of two patients who converted to full donor chimerism developing severe acute GVHD (steroid responsive, with subsequent development of fatal sepsis). An acute clinical syndrome termed "haplo immunostorm" likely secondary to cytokine flux (characterized by 1 or more of the following: fever, malaise, LFT abnormalities, rash and diarrhea) was seen commonly at the higher dose levels and was exquisitely responsive to steroids. This study demonstrated the biological activity and manageable safety profile of this approach. The minimum CD3+ T-cell dose (not CD8+ depleted) required for response in that study was $1\times10^8$ cells/kg.

Example 7—Patent Selection

Patients must have pathologically confirmed: Myelodysplastic syndrome (MDS), IPSS score of Int-2 or high (using IPSS scoring system). Patients must have failed or be ineligible or intolerant of treatment with 5-azacitidine.

Example 8—Treatment Plan

All patients will require documentation of a detailed history and physical examination and standard evaluation of cardiac, liver and renal function. All patients will undergo a bone marrow aspirate and biopsy for morphological, cytogenetic (if applicable) and flow cytometric (if applicable) evaluation no more than one month prior to registration on protocol, along with other standard disease evaluations (e.g., CT of chest, abdomen, pelvis) where applicable.
Pre-Treatment Evaluation Cyclophosphamide will be administered as an iv infusion over 1-2 hr, (depending on volume) on days -2 and -1. The dose of cyclophosphamide is 50 mg/kg/day. Dose is calculated based on the adjusted ideal body weight or actual body weight whichever is less. Body weight and height are measured directly. An approximate weight for height would be calculated from a standard table or equations that reflect ideal "values".

Cyclophosphamide and Pre-DLI Regimen

Patients will be instructed to increase fluids overnight before cyclophosphamide administration. Hydration with normal saline at 3 cc/kg/hr iv will be started 2 hr prior to cyclophosphamide, then the rate will be reduced to 2 cc/kg/hr. for 1 hr. precyclophosphamide and continued for 8 hr. post-cyclophosphamide. Mesna will be given in divided doses iv 30 min pre- and at 3, 6, and 8 hr. post cyclophosphamide.

Mesna dose will be based on the cyclophosphamide dose being given. The total daily dose of Mesna is equal to 80% of the total daily dose of cyclophosphamide.

Prophylactic anti-microbial therapy will be started on Day 0 and will follow institutional practice.

Antifungal prophylaxis will be administered as follows: Fluconazole 400 mg po or IV qd, beginning Day 0 and continuing until the ANC is >500 for 3 consecutive days (or for 2 consecutive measurements over a 3 day period). Another appropriate prophylactic antifungal agent may be substituted. *Pneumocystis carinii* pneumonia (PCP) prophylaxis will start on Day 0 and should continue until Day 60. Patients intolerant of trimethoprim/sulfamethoxazole (Bactrim) will receive either dapsone or pentamidine as PCP prophylaxis. Viral prophylaxis will consist of valacyclovir or acyclovir from Day 0 to Day 60. An oral quinolone (e.g., moxifloxacin or norfloxacin) will be administered according to institutional preference until the ANC is >500 for 3 consecutive days (or for 2 consecutive measurements over a 3 day period) following DLI.

All patients will receive infusion of haploidentical PBCs depleted of CD8+ T cells using the CliniMACS® system with CliniMACS® CD8 reagent. The numbering of the dose levels is from the lowest to the highest cell dose. The first cohort of patients (dose level 1) will receive Cy plus CD8+ T cell-depleted haploidentical PBCs (CD8− PBCs) containing an intended dose of $1\times10^5$ CD4+ T cells/kg of recipient IBW. If criteria for dose escalation are met, patients on dose level 2, 2b, 3, or 4 will receive CD8− PBCs containing an intended dose of $1\times10^6$, $3\times10^6$, $1\times10^7$, or $5\times10^7$ CD4+ T cells/kg, respectively.

DLI Dose Calculation

The formula for calculating the volume of final (CD8-depleted) product that will deliver the intended dose of CD4+ T cells is as follows: Intended volume (ml)=Intended CD4+ T cell dose (cells/kg)×Recipient IBW*(kg)/CD4+ T cell concentration (cells/ml) *Note—If actual weight <ideal, use actual weight.

However, the total number of CD8+ T cells that are infused may not exceed 3.2% of the intended number of CD4+ T cells to be infused (the numerator of the equation above). If the ratio of CD4+/CD8+ cells in the depleted product is less than 31.25 (=1/0.032), then the volume of the product to be infused will be determined by the following formula: If CD4/CD8 ratio of final product <31.25, then: Infused volume (ml)=Intended volume×(CD4/CD8 ratio)/31.25 If the ratio of CD4+/CD8+ cells in the depleted product is equal to or greater than 31.25, then the volume of the product to be infused is the intended volume (formula 1): If CD4/CD8 ratio of final product >31.25, then: Infused volume (ml)=Intended volume Transfusion Support Platelet and packed red cell transfusions will be given per current institutional recommendations.

Example 9—Duration of Therapy

Patients are eligible for only one lymphocyte infusion. This restriction is in place because rejection of the infused lymphocytes is expected to induce anamnestic immunity to cells of the donor or even to other close relatives. Patient's peripheral blood will be obtained on day 60 and tested for the presence of human anti-mouse antibody (HAMA) and for cytotoxic antibodies against donor cells.

Duration of Follow Up

Patients will be followed for a minimum of 60 days after DLI, and then until death or disease progression, whichever occurs first. Patients removed from study for unacceptable adverse events or who develop treatment-related adverse events will be followed until resolution or stabilization of the adverse event.

Post DLI Monitoring:

Patients remaining on study will have blood drawn on days 14, 28, and 60, and six months after DLI. A CBC with manual differential will be obtained with these blood draws. Lymphocyte subsets, including the percentage of cells expressing CD4 or CD8, will be analyzed by flow cytometry. After day 60, the patient will have monthly complete blood counts with white blood cell differential as long as there is no documented disease progression, until 6 months after DLI.

Disease Assessment.

In addition to disease assessments specified above, results of additional disease assessments performed as standard of care will be collected for study purposes until death or disease progression, whichever occurs first.

Example 10—Dosing Delays/Dose Modification

Cyclophosphamide dose will not be modified. DLI dose will be modified in the event of excessive content of CD8+ T cells.

Adverse Events: List and Reporting Requirements

The following information shall be collected on all patients with acute GVHD:

Date of onset (defined as the date of first biopsy confirming GVHD) GVHD evaluation form at the time of onset, weekly until GVHD resolves, and Day 60 Initial overall clinical grade Maximum overall clinical grade Date of onset of grade III-IV acute GVHD, if any.

The occurrence and severity of acute and chronic GVHD after Day 60 will be captured at the patient's six month evaluation.

All instances of grade II-IV acute GVHD will be captured as adverse events. Grade III-IV GVHD will be reported as a serious adverse event.

DLI-induced aplasia is defined as neutropenia (absolute neutrophil count <500/ml) with any evidence of donor chimerism on day 60 or later. All cases of DLI-induced aplasia will be reported as serious adverse events.

Example 11—Pharmaceutical Information

Cyclophosphamide (Cytoxan®)

Cyclophosphamide is commercially available. Cyclophosphamide is an alkylating agent which prevents cell division primarily by cross-linking DNA strands. Cyclophosphamide is cell cycle non-specific. Cyclophosphamide for injection is available in 2000 mg vials which are reconstituted with 100 ml sterile water for injection. The concentration of the reconstituted product is 20 mg/ml. The calculated dose will be diluted further in 250-500 ml of Dextrose 5% in water. Each dose will be infused over 1-2 hr. (depending on the total volume).

Clinical toxicities of cyclophosphamide include alopecia, nausea and vomiting, headache and dizziness, hemorrhagic cystitis, cardiotoxicity, immunosuppression, myelosuppression, pulmonary fibrosis, increased hepatic enzymes and syndrome of inappropriate anti-diuretic hormone (SIADH). Cyclophosphamide will be dispensed by the Oncology Pharmacy and is produced by Mead Johnson Pharmaceuticals.

Mesna (Sodium-2-Mercapto Ethane Sulphonate)

Mesna is a prophylactic agent used to prevent hemorrhagic cystitis induced by the oxasophosphorines (cyclophosphamide and ifosphamide). It has no intrinsic cytotoxicity and no antagonistic effects on chemotherapy. Mesna binds with acrolein, the urotoxic metabolite produced by the oxasophosphorines, to produce a non-toxic thioether and slows the rate of acrolein formation by combining with 4-hydroxy metabolites of oxasophosphorines.

Mesna is available in 200 mg, 400 mg and 1000 mg vials containing a 100 mg/ml solution. Each dose of mesna will be diluted further in 50 ml of normal saline to be infused over 15 min. Mesna dose will be based on the cyclophosphamide dose being given. The total daily dose of Mesna is equal to 80% of the total daily dose of cyclophosphamide. At the doses used for uroprotection Mesna is virtually non-toxic. However, adverse effects which may be attributable to Mesna include nausea and vomiting, diarrhea, abdominal pain, altered taste, rash, urticaria, headache, joint or limb pain, hypotension and fatigue.

CBER IDE Device

Donors will have their blood collected via peripheral whole blood collection (450 ml into CPDA-1) or a leukapheresis procedure to collect peripheral white blood cells under steady state conditions (without mobilization). Each leukapheresis collection will be performed on a continuous flow cell separator (COBE Spectra, Gambro) using institutional standard operating procedures for lymphocyte collection. The method of blood donation, phlebotomy versus leukapheresis, will be determined by obtaining a peripheral blood absolute CD4+ T cell count within 30 days prior to donation and by estimating the volume of blood required to obtain the targeted CD4+ T cell dose. Since the normal range of peripheral blood CD4+ T cell counts is $0.5-1.5 \times 10^6$/ml, it is likely that simple phlebotomy will be sufficient for dose levels 1-2, pheresis may be required for levels 2b but leukapheresis will be required for dose level 3 and 4.

Based upon extensive prior experience, a 4 hour leukapheresis procedure should be sufficient to obtain $5 \times 10^7$ CD4+ T cells/kg of recipient IBW. Target collections will be at least 30% more than the desired dose to accommodate for cell loss during the depletion process.

The product will undergo CD8 depletion in the Graft Engineering Laboratory. All standard operating procedures will be followed. The product will be analyzed for nucleated cell count, CD3, CD4, CD8, CD16, and CD56. The product will be stored overnight and CD8 depletion will take place on the CliniMACS® Selection System (Miltenyi Biotec, Auburn, CA). Prior to CD8 depletion, whole blood products will initially be processed to prepare a buffy coat concentrate and for major ABO incompatible donor/recipient pairs the buffy coat concentrate will be further processed using lymphocyte separation medium to remove contaminating red blood cells. Processed whole blood products or apheresis products are then concentrated and resuspended in PBS/EDTA supplemented with 0.5% human serum albumin.

Murine monoclonal CD8 antibody, conjugated to iron-dextran super-paramagnetic particles is added and incubated at room temperature for 30 minutes. One vial of antibody will be used to treat up to $40 \times 10^9$ total white blood cells and up to $4 \times 10^9$ CD8+ cells. Excess antibody will be removed by washing 1 time and the product volume will be adjusted to 100 ml with PBS/EDTA with albumin. It is then connected to the CliniMACS Selection System using a sterile disposable tubing set. The run is initiated by a pre-set computer program which controls (i) the flow of antibody-treated cells, (ii) washing that removes residual unbound cells, (iii) removal of the magnetic field around the column to release selected cells, and (iv) the final collection of CD8 depleted cells into a bag. The entire process takes approximately 2-6 hours from completion of initial product concentration. The subsequent product will be analyzed for cell count, viability, CD3, CD4, CD8, CD16, and CD56 content. The CD4 concentration will be used to calculate the patient dose. The calculated volume will be removed and prepared for infusion according to institutional standard operating procedures.

Correlative/Special Studies
Phenotypic Immune Reconstitution

Peripheral blood concentrations of lymphocyte subsets including CD4+ and CD8+ T cells will be determined using the absolute lymphocyte count and flow cytometry on days 14, 28, 60, and 6 months after DLI.

Analysis of Host CD8+ T Cell Repertoire Diversity by Spectratype Analysis. Recent studies indicate that the diversity of the T cell repertoire can be assessed by T cell receptor V_region spectratyping, which evaluates the CDR3/diversity/joining regions (Vf3-D-J-Cf3) of cells expressing a given V_gene. This region confers specificity of the T cell receptor. Immunoscoping or V_spectratyping is remarkably useful for evaluating antitumor immune responses following therapy and immune reconstitution following bone marrow transplantation49. Moreover, spectratype analysis of MDS patients before and after immunosuppressive therapy has revealed skewing of the T cell repertoire that normalizes with a response to treatment. We therefore hypothesize that patients with MDS and possibly CMML will have skewed T cell repertoires prior to treatment, that the DLI will initially induce a population of alloreactive T cells, and that responders will eventually acquire a normal T cell repertoire as revealed by spectratype analysis. Pre-treatment CD8+ T cells will be obtained from patient peripheral blood mononuclear cells (PBMCs). To identify patient anti-donor reactive T cells, pre-treatment PBMCs from the patient will be cultured for seven days with irradiated donor PBMCs prior to cell sorting. The culture period allow for the clonal expansion of patient anti-donor T cells. PBMCs will also be collected and CD8+ T cells will be purified on days 14, 28, 60, and at six months.

Example 12—NEDLI Model to Augment Anti-Tumor Effect

Exhaustion of neoAg-specific CD8+ T cells is a major barrier to the successful immunotherapy of cancer in humans. Current efforts to overcome this barrier have been directed to the use of the immune checkpoint inhibitors (CIs), alone or in combination with agents designed to alter the tumor immune microenvironment. To date, these efforts have had only modest success and so most cancer patients are unable to derive benefit from immunotherapeutic strategies. CD4+ T cells are not only able to prevent CD8+ T cell exhaustion but they are able to reverse established exhaustion and thereby restore the anti-cancer immune response. CD4+ T cells provide help to CD8+ T cells by licensing antigen-presenting cells (APCs) through the CD40 molecule on the APC. CD4+ T cell help is required for the generation of CD8+ T cell memory and to prevent CD8+ T cell exhaustion. Importantly, for help to be delivered the CD4+ and CD8+ T cells do not have to be seeing the same antigen, but they must be seeing antigens presented on the same APC. Evidence is beginning to emerge that CD4 help can reverse established exhaustion, but growing cancers induce tolerance in tumor-specific CD4+ T cells and to date there are no known strategies for reversing tolerance in CD4+ T cells to restore their helper function for CD8+ T cells. Agonistic antibodies against the CD27 molecule can recapitulate some aspects of CD4+ T cell help and so can stimulate anti-tumor immunity, especially in combination with CIs, but it is unlikely that they can reverse established T cell exhaustion against well-advanced cancers.

To reverse T cell exhaustion in cancer an infusion of MHC-alloreactive CD4+ T cells from a healthy donor can promote the regression of established cancers, despite the eventual rejection of the infused cells, by a mechanism that requires recipient CD8+ T cells. Vaccination of a healthy allogeneic donor with a viral antigen augments the therapeutic efficacy of non-engrafting donor lymphocyte infusion (NEDLI) against a tumor expressing the antigen, therefore sporadic human cancers could be treated with CD4+ T cells from healthy donors vaccinated against a tumor neoantigen.

CD4+ T cells reverse CD8+ T cell exhaustion by licensing APCs. CD4+ T cells provide help to CD8+ T cells by licensing APCs and CD4+ T cell help reverses CD8 T cell exhaustion, but it is unclear whether CD4+ T cells can reverse exhaustion by licensing APCs. The antitumor effect of NEDLI could be augmented by vaccinating donors against CD4 neoepitopes. Donor vaccination can augment the anti-tumor effects of alloBMT, and healthy donor CD8+ T cells respond vigorously to neoantigens, but CD4 neoepitopes are difficult to identify. An already validated CD4 neoepitope, M30 will be used to demonstrate proof of principle while technology for identifying CD4 neoepitopes advances.

Currently available cell therapies of cancer (allogeneic blood or marrow transplantation, CAR T cells or T cell-receptor modified T cells, tumor-infiltrating lymphocytes) employ infusion of lymphocytes that directly kill cancer cells. In contrast, the goal of NEDLI is to revive endogenous anti-tumor immunity by providing helper signals through recipient antigen-presenting cells (APCs). The hypothesis that transiently engrafting CD4+ T cells can reverse exhaustion in neoAg-specific CD8+ T cells is thoroughly novel. U.S. Pat. No. 9,931,359 B2 describes a method of selecting HLA Class II mismatched donors for CD8-depleted non-engrafting donor lymphocyte infusion to revive endogenous anti-tumor immunity. In the present application, the donor has at least one HLA Class II allele match with the recipient, the donor has been vaccinated against a tumor or viral neoantigen, and then the virus-specific or tumor-specific T cells are expanded further ex vivo.

The anti-tumor effect of the therapy is augmented by an MHC Class II mismatch in the graft-versus-host direction to ensure a high frequency of alloreactive donor memory CD4+ T cells (via heterologous immunity, as memory but not naïve CD4+ T cells can overcome tumor-induced immunosuppression and deliver the appropriate helper signals. Exogenous CD4+ T cell help could revive CD8+ T cells against multiple neoepitopes through epitope spreading (see FIG. 12) so that the targeted antigen would not have to be expressed in all cancer cells.

Figure 5:
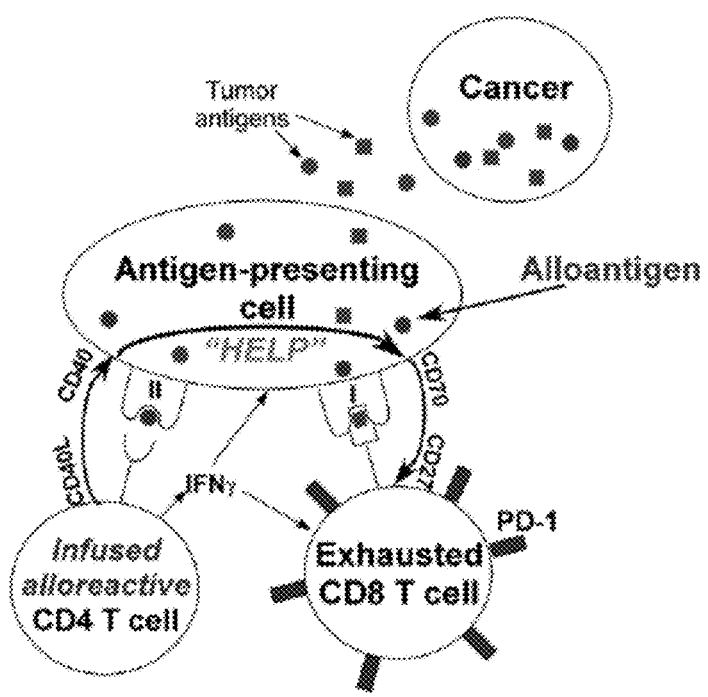
FIG. 5 shows a model to explain anti-tumor efficacy of transiently engrafting, MHC-mismatched donor lymphocyte infusions.

Disease responses induced by transiently engrafting lymphocytes could "be explained best by an indirect process initiated by the short-lived donor cells but carried to completion by the cells of the host". The finding of the present invention is that treatment of mice with cyclophosphamide (Cy) followed by CD8+ cell-depleted MHC-mismatched donor lymphocyte infusion (Cy+CD8− DLI) induces regression of established tumors with minimal toxicity in models of both hematologic and solid cancers, even though the donor cells are eventually rejected by the host immune system. The optimal antitumor effect of Cy+CD8− DLI required the presence of donor CD4+ T cells, host CD8+ T cells, and alloantigen expression by normal host but not tumor tissue. Importantly, depletion of CD8+ cells from the DLI abrogated the risks of sustained donor cell engraftment and lethal GVHD but did not compromise anti-tumor efficacy. Based upon these results, a model (FIG. 5) was proposed in which alloreactive donor CD4+ T cells reverse exhaustion in tumor-specific, recipient CD8+ T cells by delivering signals through APCs that cross-present tumor antigens. As illustrated in FIG. 5, the proposed mechanism for the reversal of exhaustion by infused, alloreactive Type 1 ($T_h1$) CD4+ T cells. Recognition of major histocompatibility complex (MHC) Class II alloantigen on the surface of a recipient antigen presenting cell (APC) leads to activation of the alloreactive donor CD4+ T cell with subsequent upregulation of activation ligands including CD154, the ligand for CD40 on the APC. Ligation of CD40 induces upregulation of molecules on the APC surface, including CD70 that is the ligand for CD27 on CD8+ T cells. This signaling cascade has been shown to be required for the induction of CD8+ T cell memory; it is proposed that the same interactions are involved with the reversal of CD8+ T cell exhaustion and reversion to a CD8+ memory T cell. Interferon gamma and/or interleukin 21 secreted by the CD4+ T cell may also play a role in the reversal of T cell exhaustion.

Figure 6A:
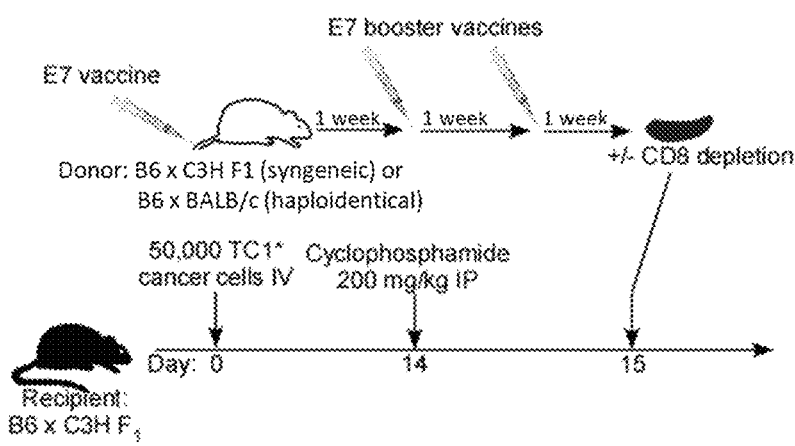
FIG. 6A illustrates the protocol used to obtain the results in FIG. 6B. C57BL/6×C3H (B6×C3H; B6C3) $F_1$ or BALB/c×C57BL/6 (BALB/c×B6; CB6) $F_1$ mice were vaccinated weekly for a total of 3 doses with 25 µg of pcDNA-3-CRT/E7 a DNA vaccine against E7 of human papillomavirus serotype 16. One week later, spleen cells from naïve or vaccinated mice were left undepleted or were depleted of CD8+ T cells and 20 million cells were infused into B6×C3H $F_1$ mice that had received 50,000 E7-expressing TC1 lung cancer cells two weeks earlier and cyclophosphamide 200 mg/kg IP one day earlier. Survival of the tumor-bearing mice is shown for recipients of syngeneic B6×C3H $F_1$ cells on the left and recipients of MHC-haploidentical BALB/c×B6 F1 cells on the right.

Though NEDLI is able to induce potent anti-tumor effects against hematologic malignancies, its effect against solid tumors is generally weaker and non-curative. Priming donors against a tumor-specific antigen could enhance the anti-tumor effect of NEDLI. To test this hypothesis, healthy syngeneic or MHC-haploidentical donors were vaccinated against the E7 antigen of human papillomavirus and spleen cells from the primed donors, either undepleted or CD8-depleted, were infused into mice that had been inoculated 14 days earlier with TC1, an E7-expressing lung cancer (FIG. 6A).

Tumor-bearing recipients were cured by undepleted DLI from E7-primed syngeneic donors (FIG. 6B, left panel), and the therapeutic effect was abrogated by CD8-depletion.

Figure 6B:
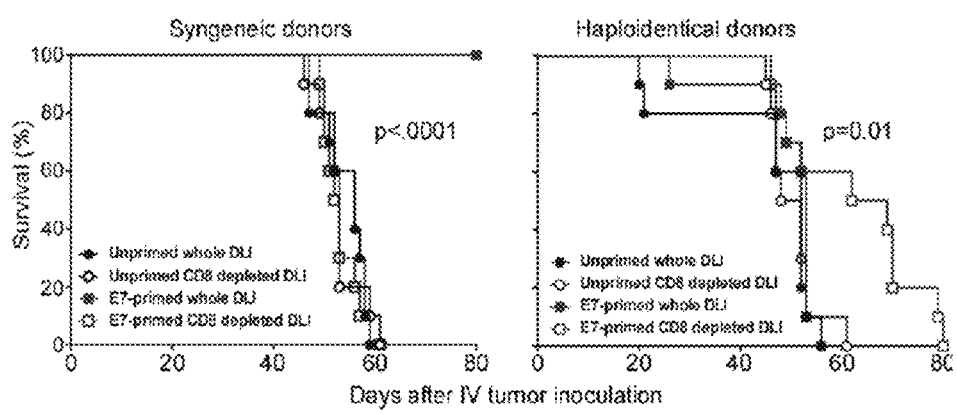

Interestingly, when haploidentical donors were used and the donor cells were rejected, a beneficial effect was obtained with CD8-depleted but not undepleted DLI from primed donors (FIG. 6B, right panel). Since CD8-depleted syngeneic DLI did not prolong survival, we conclude that alloreactive and E7-specific CD4+ T cells cooperate to induce anti-tumor immunity in the non-engrafting situation, and that alloreactive CD8+ T cells impair anti-tumor immunity, perhaps by killing the (recipient) APCs that provide the signals to reverse exhaustion in endogenous, tumor-specific CD8+ T cells.

Figure 7A:
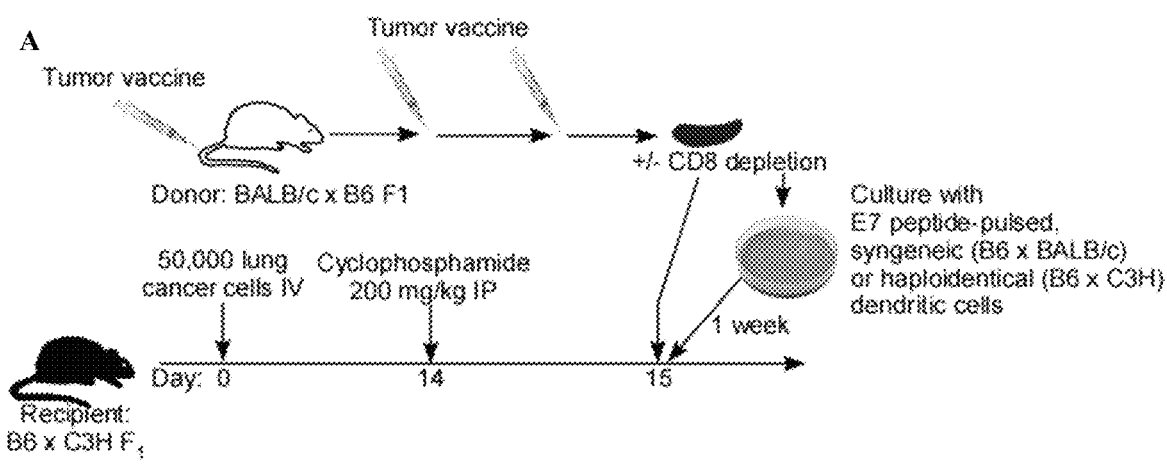
FIG. 7A illustrates the protocol used to obtain the results in FIG. 7B.

Whether the anti-tumor efficacy of NEDLI could be augmented by stimulating primed T cells ex vivo with E7-peptide pulsed dendritic cells was then tested. Spleen cells from E7-primed CB6 F1 donors were left undepleted or were CD8-depleted prior to ex vivo culture for 1 week with syngeneic CB6 F1 or haploidentical B6C3 F1 dendritic cells pulsed with overlapping pentadecamers covering the full length E7 protein of HPV16. After culture, cells were harvested and infused into TC1-bearing B6C3 F1 mice treated with Cy. FIG. 7 shows that ex vivo culture of the E7-primed donor cells with E7 peptides augments the anti-tumor efficacy of the DLI. Further, ex vivo cultured donor CD8+ T cells did not cause lethal GVHD.

Figure 7B:
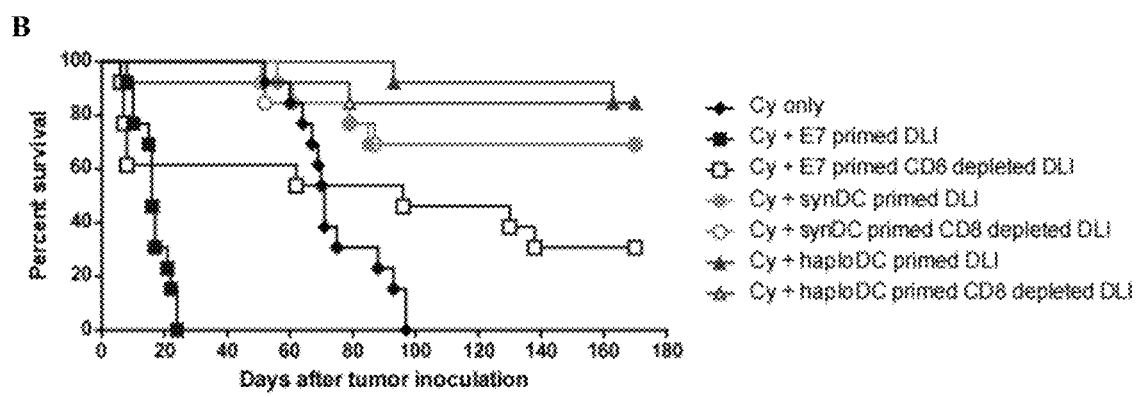
FIG. 7B shows a graph illustrating the augmentation of the anti-tumor efficacy of NEDLI by the ex vivo culture of spleen cells from tumor Ag-primed donors. Spleen cells from E7-primed CB6 F1 donors were cultured with CB6 F1 (syn) or B6C3 F1 (haplo) dendritic cells (DCs) pulsed with overlapping pentadecamers of E7 from HPV16 (JPT Peptide Tech.)
Figure 8A:
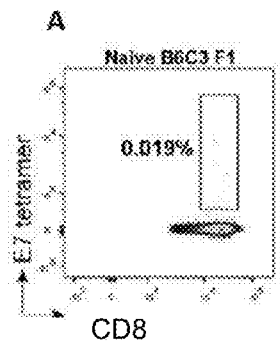
FIGS. 8A-H show percentages of recipient CD8+ T cells as obtained by flow cytometry.
Figure 8B:
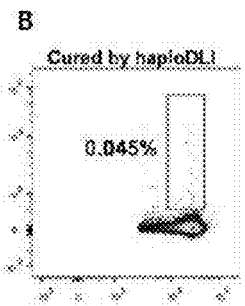
Figure 8C:
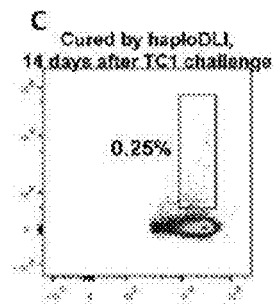
Figure 8D:
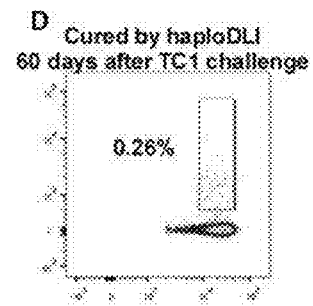
Figure 8E:
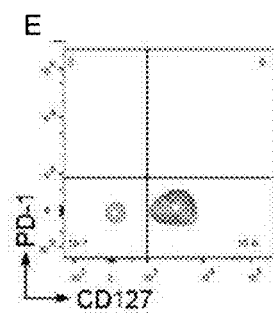
Figure 8F:
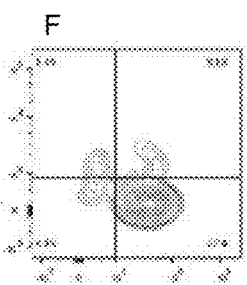
Figure 8G:
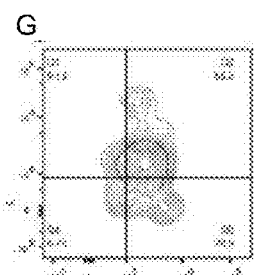
Figure 8H:
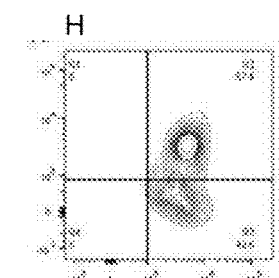

Cured mice in FIG. 7 had no evidence of donor ($H-2^d$+) chimerism but contained an expanded population of E7-specific CD8+ T cells, as demonstrated by staining with fluorochrome-conjugated tetramers of the $H-2K^b$ MHC molecule pulsed with the immunodominant $K^b$-binding peptide of E7 (FIG. 8B). This expanded population of E7-specific CD8+ T cells displayed a memory ($CD127^+PD-1^-$) phenotype (FIG. 8F). Cured animals resisted re-challenge with TC1, which elicited further clonal expansion of the E7-specific CD8+ T cells (FIG. 8C, D) and their upregulation of PD-1 expression (FIG. 8G,H).

As shown in FIG. 8, the percentage of recipient CD8+ T cells that were reactive to the immunodominant, H-2Kb-restricted peptide of E7 was determined by staining with H-2K-b tetramers pulsed with the peptide (top row). The bottom row shows cell surface expression of CD127 and PD-1 on the gated, E7-specific CD8+ T cells. Memory CD8+ T cells are CD127+ and $PD-1^{low}$; activated T cells are $CD127+PD-1^{high}$, and exhausted T cells are CD127− and $PD-1^{high}$.

Figures 9A, 9B, 9C:
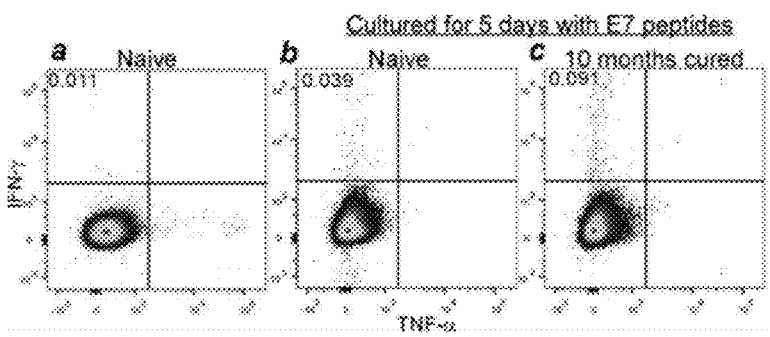
FIG. 9A shows dot-plots illustrating intracellular interferon gamma (IFNγ) and tumor necrosis factor alpha (TNFα) staining of CD4+ T cells from untreated B6×C3H F1 naïve mice five days after stimulation with unpulsed B6×C3H F1 dendritic cells.
FIG. 9B shows intracellular interferon gamma (IFNγ) and tumor necrosis factor alpha (TNFα) staining of CD4+ T cells from untreated B6×C3H F1 naïve mice five days after stimulation with DCs pulsed with E7 peptides.
FIG. 9C illustrates intracellular interferon gamma (IFNγ) and tumor necrosis factor alpha (TNFα) staining of CD4+ T cells from mice cured by non-engrafting donor lymphocyte infusion, five days after stimulation with DCs pulsed with E7 peptides.

Culture of CD8-depleted lymphocytes from cured animals (open triangles in FIG. 7) with E7 peptides revealed an expanded population of IFN-γ-secreting CD4+ T cells (FIGS. 9A and 9B). IFN-γ was also produced by culture of naïve CD4+ T cells with E7 peptides (FIGS. 9A and 0B), raising the possibility that neoAg-specific Th1 cells for adoptive immunotherapy of cancer could be expanded ex vivo from healthy, unvaccinated donors, thereby ameliorating concerns for donor safety.

Figure 9D:
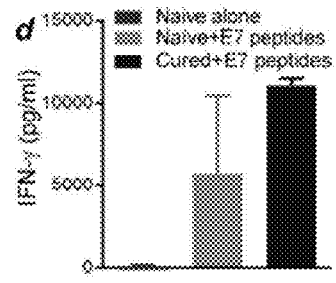
FIG. 9D shows a graph of the quantification by ELISPOT assay of the IFNγ secretion of the same cells as illustrated in FIGS. 9A-C.

As illustrated in FIG. 9, intracellular interferon gamma (IFNγ) and tumor necrosis factor alpha staining of CD4+ T cells from untreated B6×C3H $F_1$ mice (naïve; a,b) or from mice cured by non-engrafting donor lymphocyte infusion (c), five days after stimulation with unpulsed B6×C3H F1 dendritic cells (a), or DCs pulsed with E7 peptides (b,c) were measured. Panel d shows IFNγ secretion of the same cells by ELISPOT assay.

Figure 10A:
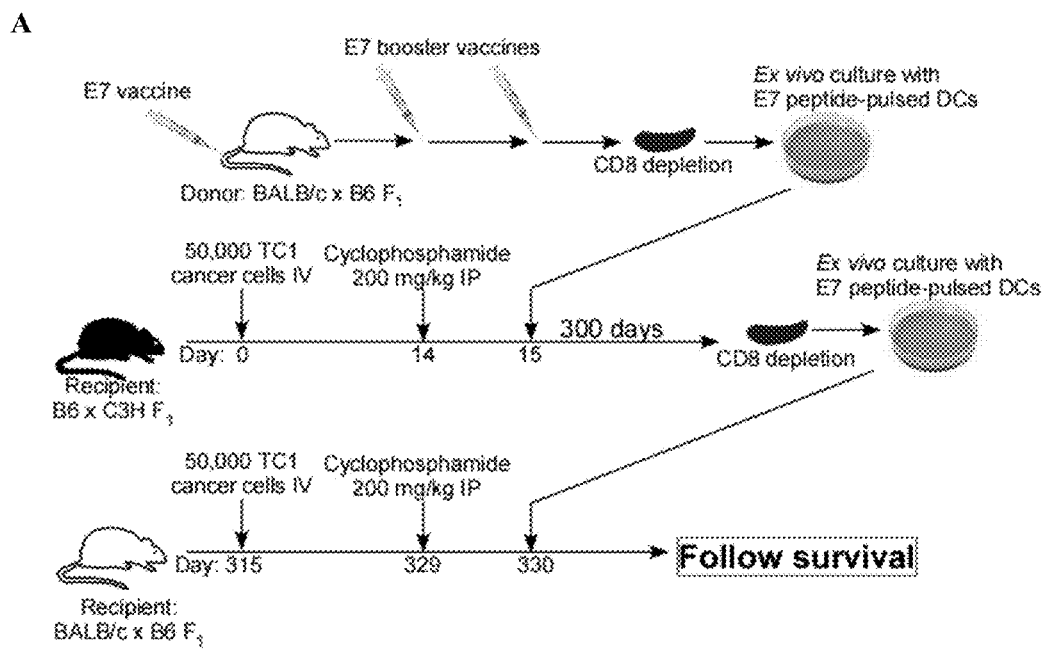
FIG. 10A illustrates the protocol used to obtain the results in FIG. 10B TCI-bearing B6×C3H $F_1$ mice were cured by cyclophosphamide plus CD8-depleted lymphocytes taken from E7-vaccinated donors and expanded ex vivo with E7 peptides. Three hundred days after the lymphocyte infusion, spleen cells from the cured mice were depleted of $CD8^+$ cells, cultured for one week with E7 peptides, and transferred (20 million cells put into culture per recipient) into TC1 bearing BALB/c×B6 $F_1$ mice treated one day earlier with cyclophosphamide. Alternatively, TC1 bearing BALB/c×B6 $F_1$ mice received spleen cells from naïve B6×C3H $F_1$ donors that were depleted of $CD8^+$ cells and cultured with E7 peptides for one week prior to adoptive transfer. Survival is shown in FIG. 10B.
Figure 10B:
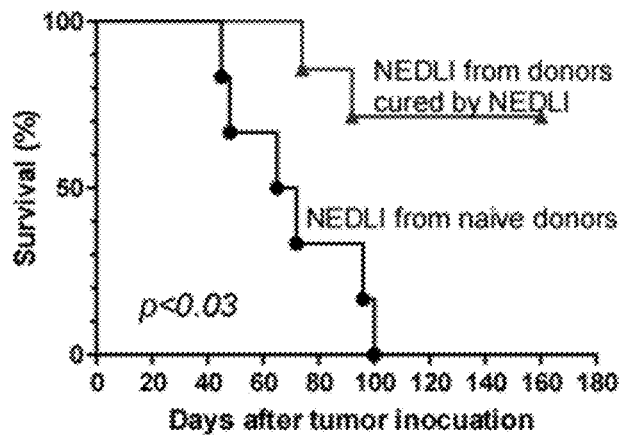

As illustrated in FIG. 10, TC1-bearing B6×C3H $F_1$ mice were cured by cyclophosphamide plus CD8-depleted lymphocytes taken from E7-vaccinated donors and expanded ex vivo with E7 peptides. Three hundred days after the lymphocyte infusion, spleen cells from the cured mice were depleted of CD8+ cells, cultured for one week with E7 peptides, and transferred (20 million cells put into culture per recipient) into TC1 bearing BALB/c×B6 $F_1$ mice treated one day earlier with cyclophosphamide. Alternatively, TC1 bearing BALB/c×B6 $F_1$ mice received spleen cells from naïve B6×C3H $F_1$ donors that were depleted of CD8+ cells and cultured with E7 peptides for one week prior to adoptive transfer. Survival is shown in FIG. 10B.

Ex vivo-cultured, CD8-depleted spleen cells from B6C3 mice cured by NEDLI were themselves able to prolong survival of mice, again despite being rejected by the tumor-bearing CB6 F1 recipients (FIG. 10B). Thus, mice cured by non-engrafting donor lymphocyte infusion contain CD4+ T cells that are able to serially transfer anti-tumor immunity when given as NEDLI.

Human papillomavirus (HPV) is associated with several human cancers including cancers of the oropharynx, uterine cervix, penis, and anus. The virus has been found to be able to transform epithelial cells via intracellular expression of two viral antigens, E6 and E7. E6 inactivates the p53 tumor suppressor protein and E7 inactivates the retinoblastoma protein, both proteins being intimately involved in the control of the cell cycle. Transformed cells are no longer subject to growth control and the E6 and E7 proteins are essential for the progression to malignancy.

The immune system is capable of reacting to and eliminating HPV. A critical determinant of whether an individual who is exposed to an oncogenic strain (usually HPV16 or HPV18) eliminates the virus or becomes chronically infected is the T cell response to HPV, more precisely the CD4+ T cell response to HPV. Individuals who make a type I CD4+ T cell response, including the production of IFN-γ, typically eliminate the virus, whereas individuals who fail to make such a type I response can become chronically infected and susceptible to malignant transformation. Investigational vaccines are now available to generate responses against the E6 and E7 antigens of HPV16 and HPV18.

In an animal model, it was found that, when the donor and recipient are matched for all genes of the major histocompatibility complex (MHC) it is possible to transfer anti-tumor immunity by vaccinating a donor against HPV E7 and transferring vaccinated donor CD4+ and CD8+ T cells to the recipient (FIG. 6B, left panel) whereas when the donor and recipient are MHC-haploidentical, it is possible to transfer anti-tumor immunity by vaccinating the donor against HPV E7 and transferring vaccinated CD4+ T cells but not vaccinated CD8+ T cells to the recipient (FIG. 6B, right panel). The anti-tumor efficacy of NEDLI from donors vaccinated against a tumor-specific antigen can be augmented by culturing the vaccinated T cells in vitro with tumor peptides prior to infusion into the recipient (FIG. 7B). The infusion of vaccinated and ex vivo-stimulated donor CD4+ T cells restores the recipient's immune response—the cured animals now have CD8+ T cells (FIGS. 8B-D) and CD4+ T cells (FIG. 9C,D) that respond to tumor antigen and reject tumor cells even though the donor cells have been eliminated. This means that the immunity to HPV has been effectively transferred from donor to recipient.

The invention contemplates the infusion of CD8-depleted cells that from donors vaccinated against a tumor-specific antigen (a viral antigen or tumor neoantigen) and cultured with peptides from the viral or neo-antigen. Alternatively, the invention contemplates the infusion of unimmunized donor CD8-depleted cells stimulated ex vivo with peptide-pulsed dendritic cells to stimulate virus-specific or neoantigen-specific CD4+ T cells. The invention also contemplates the creation of a cell bank containing HPV-primed CD4+ T cells from donors of different human leukocyte antigen (HLA) types. As an example, the table below shows that a bank of 10 cell lines, with each cell line uniquely expressing one of the ten most common HLA Class II alleles, is sufficient to provide a therapeutic for 95.7% of the US Caucasian population. HLA class II molecules include HLA-DRB1, HLA-DPB1, and HLA-DQB1, as examples.

| Allele | Frequency rank | Allele frequency | Cumulative allele frequency | Cumulative population frequency |
|---|---|---|---|---|
| DRB1*15:01 | 1 | 0.1346 | 13.5% | 25.1% |
| DRB1*07:01 | 2 | 0.1342 | 26.9% | 46.5% |
| DRB1*03:01 | 3 | 0.1216 | 39.0% | 62.8% |
| DRB1*04:01 | 4 | 0.0878 | 47.8% | 72.8% |
| DRB1*01:01 | 5 | 0.0860 | 56.4% | 81.0% |
| DRB1*13:01 | 6 | 0.0563 | 62.1% | 85.6% |
| DRB1*11:01 | 7 | 0.0556 | 67.6% | 89.5% |
| DRB1*13:02 | 8 | 0.0488 | 72.5% | 92.4% |
| DRB1*04:04 | 9 | 0.0388 | 76.4% | 94.4% |
| DRB1*11:04 | 10 | 0.0295 | 79.3% | 95.7% |

Whether the anti-tumor efficacy of NEDLI can be augmented by increasing the frequency of neoAg-specific CD4+ T cells in the infusion is the main point of investigation. Since preliminary data showed an apparent synergy between alloreactive and tumor-specific CD4+ T cells in mediating anti-tumor immunity after NEDLI, the effect of MHC mismatching in the model of donor neoAg vaccination will be tested as well. By choosing donor and recipient strains wisely, it should be easily possible to dissect out the relative roles of alloreactivity versus neoAg priming on anti-tumor effects.

Example 13—Characterization of the Effect of NeoAg Vaccination of a Healthy Donor on the Anti-Tumor Effect of NEDLI The benefit of in vivo donor vaccination versus ex vivo T cell expansion and the interaction between alloreactive and neoAg-specific T cells.

The goal of this experiment was to test two methods of augmenting CD4+ T cell help against a tumor neoAg to increase the anti-tumor efficacy of CD8− NEDLI against a "sporadic" tumor: 1) in vivo vaccination with a CD4+ T cell neoepitope, without or with subsequent neoepitope stimulation ex vivo; or 2) in vitro "priming" using serial stimulation of CD4+ T cells with neopeptide+DCs. The design of the experiment is shown in Table 3 below. The B16-F10 melanoma of C57BL/6 (B6; $H-2^b$) origin grows in F1 hybrids; immunogenic CD4+ neo-epitopes have been identified.

1) B6×C3H (B6C3; $H-2^{bxk}$) F1 or MHC-haploidentical BALB/c×B6 (CB6; $H-2^{bxd}$) F1 mice will be vaccinated with either the mutant neo-epitope M30 (groups 2,6), encoded from the Kinesin family member 18b gene (Kif18b), or with the corresponding wild type peptide (groups 1,5), the vaccine comprising 100 jtg synthetic peptide and 50 jtg poly (I:C) injected into the lateral flank in a volume of 200 jtl phosphate buffered saline. The efficacy of vaccination and the phenotype (CD4 vs CD8) of responding cells will be tested by flow cytometry and intracellular cytokine staining (ICS) for interferon gamma (IFN y) or tumor necrosis factor alpha (TNFa). Two weeks after vaccination, donor mice will be euthanized, spleen cells will be depleted of CD8+ cells and infused into B16-F10 bearing B6C3 mice treated with cyclophosphamide (Cy) the day before infusion. Alternatively, CD8-depleted cells from immunized donors will be cultured for 5 days with M30-pulsed, donor DCs for five days prior to infusion (groups 3,7);

2) Spleen cells from naïve B6C3 or CB6 F1 mice will be stimulated weekly×2 with M30-pulsed autologous dendritic cells plus 20 U/ml IL-2 (groups 4,8). The frequency of M30-specific, IFN'γ+ CD4+ T cells will be measured by ICS before and after ex vivo stimulation. NeoAg-specific CD4+ T cells can be purified using the IFN'γ capture assay (Miltenyi Biotec) and expanded further using beads coated with anti-CD3 and anti-CD28.

TABLE 3

| Group | Recipient strain | N | $10^5$ B16-F10 IV d 0 | Cy 200 mg/kg IP d 14 | Donor strain | $2 \times 10^7$ CD8⁻ spl cells IV d 15 |
|---|---|---|---|---|---|---|
| 1 | B6 x C3H F1 | 14 | + | + | B6C3 F1 | WT* primed |
| 2 | " | 14 | + | + | " | Mut* primed |
| 3 | " | 14 | + | + | " | Mut primed + ex vivo cultured |
| 4 | " | 14 | + | + | " | Ex vivo culture with M30 x 2 |
| 5 | " | 14 | + | + | CB6 F1 | WT primed |
| 6 | " | 14 | + | + | " | Mut primed |
| 7 | " | 14 | + | + | " | Mut primed + ex vivo cultured |
| 8 | " | 14 | + | + | " | Ex vivo culture with M30 x 2 |

*WT = PSKPSFQEFVDWEKVSPELNSTDQPFL (SEQ ID NO: 1);
Mut (M30) = PSKPSFQEFVDWENVSPELNSTDQPFL (SEQ ID NO: 2)

Based on past data in similar treatment groups, a non-parametric Mann-Whitney test for comparing the two treatment groups was simulated. For a power of 80%, with a two-sided type-I error of 0.05, it was estimated that a sample size of 14 per treatment group should be sufficient.

The benchmark for success will be a significant prolongation of survival in recipients of CD8-depleted cells containing an expanded (by vaccination or ex vivo culture) population of M30-specific CD4+ T cells (compare groups 6, 7, or 8 to 5), reflecting the benefit of getting CD4+ T cell help to the tumor microenvironment, where they can re-program myeloid cells to become more immunostimulatory as well as provide help for CD8+ T cells. Alloreactivity of the donor population will likely augment the anti-tumor efficacy of primed NEDLI (e.g. compare group 6 to 2, 7 to 3, and 8 to 4). It is possible that a single neoAg, a single dose of vaccine, or the vaccine formulation is insufficient to augment anti-tumor immunity. If no prolongation of survival is achieved, donors will be vaccinated with mRNA pentatope vaccines. Donor vaccination could exacerbate GVHD or cytokine release syndrome; this could be mitigated by reducing the dose of donor cells.

Comparison the anti-tumor effects of neoAg-primed NEDLI versus immunologic checkpoint blockade (ICB), alone or in combination. A recent report showed that intratumoral delivery of a recombinant adenovirus encoding CD40 ligand, a key molecule involved in the delivery of CD4+ T cell help (FIG. 5), was superior to yet synergistic with combined ICB with anti-PD-1+anti-CTLA4 antibodies against subcutaneous B16-F10. We predict that neoAg-primed NEDLI will be superior to and synergistic with ICB. Sixty-five B6C3 F1 mice will each be inoculated with $5 \times 10^5$ B16-F10 melanoma cells subcutaneously on the flank on day −8 and will receive Cy 200 mg/kg IP on day 0. On day 1, groups of thirteen mice each will receive treatment with either: 1) nothing; 2) 20 million CD8-depleted spleen cells from unprimed CB6 F1 donors (which provides a modest but significant survival benefit); 3) 20 million CD8-depleted spleen cells from M30 peptide-(see expt 1) vaccinated CB6 F1 donors; 4) ICB with 200 jtg each of monoclonal antibodies against mouse PD-1 (clone RMPI-14) and CTLA-4 (clone 9H10, both from Bio X Cell) given intraperitoneally every 3 days for 4 doses; or 5) M30-primed, CD8-depleted CB6 F1 spleen cells plus ICB. Tumor growth will be measured thrice weekly on seven mice per group. To examine the effect of NEDLI on endogenous, tumor-specific CD8+ T cells, the phenotype and function of $H-2K^b$-restricted CD8+ T cells specific for the p15E peptide (KSPWFTTL) of gp70 a retroviral protein expressed in B 16-F10 but not in normal tissues of the C57BL/6 mouse will characterized. On each of treatment days 7 and 14, three mice per group will be sacrificed, and single cell suspensions from spleen, tumor-draining lymph node, and disaggregated tumor will be stained with fluorochrome-conjugated tetramers of $H-2K^b$ loaded with the p15E peptide (MBL International, Woburn, MA) as well as antibodies against CD62L, $T_{bet}$, CD127, CD27, and KLRG-1. The tumor microenvironment will characterized by assessing CD11c+ myeloid cell expression of CD80, CD86, and PD-L1 and characterize the ratio of Foxp3+ Tregs to total CD4+ T cells, and the CD8/Treg ratio. TILs as well as lymph node and spleen cells will stimulated with the p15E peptide and IFN-γ, TNF-α, and granzyme B production by intracellular cytokine will be characterized by staining and flow cytometry. NeoAg priming is expected to augment the anti-tumor efficacy of NEDLI as reflected by slower sc tumor growth and enhanced activation of tumor-specific CD8+ T cells. Since there is evidence that CD4+ T cell help reverses CD8+ T cell exhaustion but ICIs do not, we predict that neoAg-primed NEDLI will have superior anti-tumor efficacy to ICIs.

A mixed effects model analysis using the MIXED procedure in SAS (Cary, NC) and the parametric residual resampling method of Westfall and Young using the Glinmix procedure to adjust the post hoc testing to be limited to only the interesting comparisons. Flow cytometry data will be expressed as mean % of positive cells, or mean fluorescence intensity (MFI) with confidence intervals. Group means will be compared using the Mann-Whitney U test.

Example 14—Characterization of how NEDLI from Virus-Antigen or NeoAg-Primed Donors Induces Tumor Immunity Whether alloreactive donor CD4+ T cells augment anti-tumor immunity by providing signals through recipient APCs to tumor-specific, recipient CD8+ T cells will be determined.

Previous studies have shown that the therapeutic effect of MHC-mismatched, CD8-depleted donor lymphocyte infusion requires donor CD4+ T cells, recipient CD8+ T cells, and alloantigen expression on normal host tissue cells. Based upon these results, it is hypothesized that alloreactive CD4+ T cells reverse exhaustion of tumor-specific CD8+ T cells by licensing APCs. If so, then the antigens that are being recognized by the CD4+ and the CD8+ T cells must be presented on the same APC.

Figure 11A:
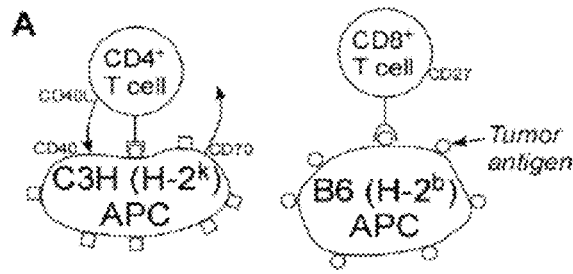
FIG. 11A shows a schematic representation of biparental bone marrow chimeras to determine the requirement APC licensing in tumor immunity.
Figure 11B:
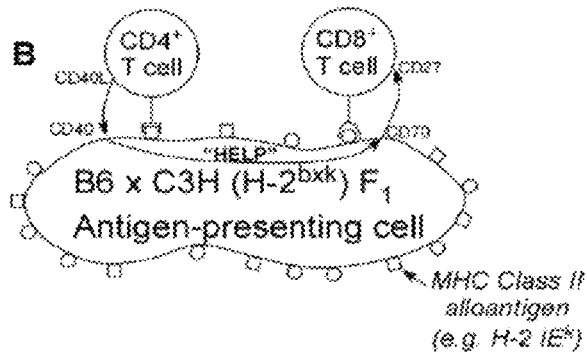
FIG. 11B shows a schematic representation of F1 bone marrow chimeras to determine the requirement APC licensing in tumor immunity.

The key to this experiment is to segregate alloantigen and tumor antigen presentation onto different APCs to prevent CD4+ and CD8+ T cells from communicating. This is done by making biparental bone marrow chimeras (depicted in FIG. 11A; and groups 3 and 4 in Table 4 below), in which one parental strain, B6 ($H-2^b$), can present tumor antigen to tumor-specific, $H-2^b$ restricted CD8+ T cells, while the other strain, C3H, presents MHC Class II alloantigen (H-2 $I-A^k$ or $I-E^k$) to non-engrafting donor CD4+ T cells. The positive control for this experiment is to make F1-parent chimeras (FIG. 11B; and groups 5 and 6 below), in which case the APCs can present both alloantigen to CD4+ T cells and neoantigen-specific CD8+ T cells, and so can act as a bridge for these T cells to communicate.

Methods: Irradiated (950 cGy) B6 mice will be transplanted with $10^7$ T cell depleted ($T^-$) B6C3 F1 bone marrow (BM) cells (groups 3 and 4) or with a mix of $5×10^6$ T-B6 and $5×10^6$ T- C3H ($H-2^k$) BM cells. Two months later, chimeras will be given $5×10^4$ E7-expressing TC1 ($H-2^b$) lung cancer cells IV. Two weeks later, the tumor-bearing recipient will be treated with Cy 200 mg/kg IP followed the next day by nothing or with ex vivo E7-peptide stimulated, CD8$^-$ spleen+LN cells from E7-immunized donors (open triangles in FIG. 7). Survival of different groups will be compared by the Log Rank test.

Groups 1 and 2 are the negative controls for this experiment, as B6 APCs cross-present tumor antigen but there is no alloantigen to stimulate donor CD4+ T cell help. MHC Class II alloantigen and tumor antigen are presented on different APCs in groups 3 and 4 but on the same APCs in groups 5 and 6. If alloreactive donor CD4+ T cells augment endogenous anti-tumor immunity by licensing APCs, then mice in group 6 will survive significantly longer than mice in group 4. If alloreactive donor CD4+ T cells prolong survival exclusively by secreting cytokines following allorecognition, then the survival of mice in group 4 and 6 should be roughly equivalent but superior to the survival of mice in group 2.

If exogenous help reverses exhaustion through APC licensing, then group 4 reduces to syngeneic CD8-depleted DLI, which was ineffective (FIG. 6, left panel, open red squares). Comparing Cy only (FIG. 7, black diamonds) to CD8$^-$ DLI stimulated ex vivo with peptide-pulsed haploDCs (open red triangles; analogous to group 6) yields a hazard ratio of 15. For a two-sided type-I error of 0.05 and a sample size of 10 in each group, power=0.999, thus 10/group is more than sufficient to test the main hypothesis.

Evaluation of NEDLI Capability to Induce Epitope Spreading.

Figure 12:
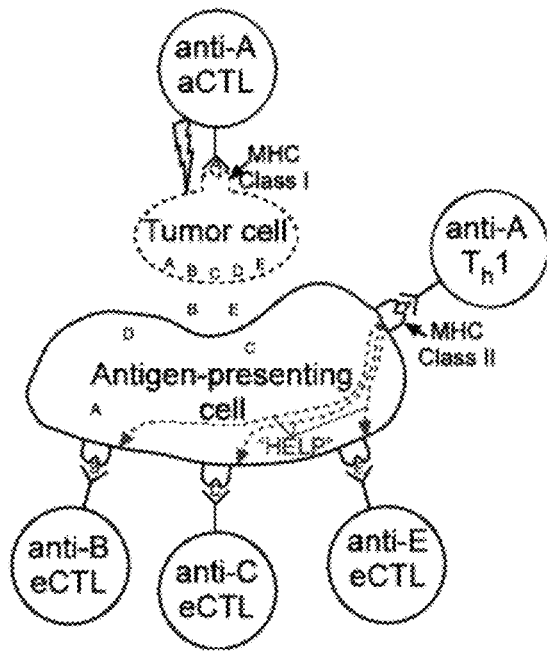
FIG. 12 shows a schematic illustrating how $CD4^+$ T cell help reverses exhaustion in $CD8^+$ T cells (eCTL) specific for neoantigens B, C, and E, liberated by dying tumor cells.

Intratumoral clonal heterogeneity and HLA or neoAg loss may limit the efficacy of immunotherapies directed against a single tumor antigen (e.g. CAR T cells, anti-tumor monoclonal antibodies, tumor vaccines). Epitope spreading counteracts tumor evasion by broadening the response to antigens not directly targeted by the therapy. it is hypothesized that CD4+ T cell help promotes epitope spreading by reversing exhaustion in neoAg-specific CD8+ T cells (FIG. 12). FIG. 12 illustrates the postulated mechanism of epitope spreading following infusion of transiently engrafting, tumor-specific CD4+ T cells. Killing of tumor cells by CD8+ cytotoxic T cells (CTLs) specific for antigen "A", leads to the release and cross-presentation of antigens A-E by antigen-presenting cells in the tumor microenvironment. Infused, type I (Th1) CD4+ T cells recognize antigen A presented by MHC Class II molecules and provide signals to reverse exhaustion in CD8+ T cells (eCTL) recognizing antigens B, C, and E presented in the context of MHC Class I molecules on the same antigen-presenting cell.

The following experiment is designed to test this hypothesis.

OT-I transgenic mice (Jackson Labs) contain CD8+ T cells encoding a transgenic T cell receptor for chicken ovalbumin (OVA) peptide 257-264 (SIINFEKL, SEQ ID NO: 3) presented by the H-2 $K^b$ MHC Class I molecule, whereas OT-II mice (Jackson Labs) contain CD4+ T cells specific for OVA peptide 323339 (ISQAVHAAHAEINEAGR, SEQ ID NO: 4) presented by H-2 $I-A^b$. B16-OVA is the MHC Class II-negative B16-F10 melanoma line that has been engineered to express chicken ovalbumin, and so is recognized by OT-I T cells. B6.SJL×C3H ($H-2^{kxb}$, CD45.1+), OT-I×C3H ($H-2^{kxb}$, CD45.1-), and OT-II×BALB/c ($H-2^{dxb}$) F1 mice will be generated by breeding the corresponding inbred strains. Eighty-one B6.SJL×C3H F1 mice will each receive 2 million CD8+ T cells IV from the OT-I×C3H F1 mice, and two days later will be inoculated subcutaneously with $5×10^5$ B16-F10 melanoma cells on one flank and 5×105 B16-OVA cells on the opposite flank. When tumors have grown to approximately 5 mm on each side, three mice will be euthanized for studies below, and 13 mice per group will receive Cy 200 mg/kg IP followed one day later by either: 1) nothing; 2) 20 million CD8-depleted spleen cells from CB6 F1; $H-2^{dxb}$) mice primed two weeks earlier with the Kif18b-encoded wild-type peptide (PSKPSFQEFVDWEKVSPELNSTDQPFL, SEQ ID NO: 5; see experiment 1 for details of vaccination); 3) 20 million CD8-depleted spleen cells from CB6 F1 mice primed two weeks earlier with the M30 (PSKPSFQEFVD-WENVSPELNSTDQPFL, SEQ ID NO: 6) neoepitope; 4) CD8-depleted spleen cells containing 1 million CD4+ T cells

| Group | N | Recipient | $5 × 10^4$ TC1 IV day 0 | Cy 200 mg/kg IP day 14 | E7-primed + ex vivo stimulated, CD8$^-$ CB6 F1 |
|---|---|---|---|---|---|
| 1 | 10 | B6 – B6 | + | + | – |
| 2 | 10 | " | + | + | + |
| 3 | 10 | (B6 + C3H) – B6 | + | + | – |
| 4 | 10 | " | + | + | + |
| 5 | 10 | B6 × C3H (B6C3) F1 – B6 | + | + | – |
| 6 | 10 | " | + | + | + | from unimmunized OT-II×BALB/c F1 mice; 5) CD8-depleted spleen cells taken from OT-II×BALB/c mice and cultured for 5 days with OVA323-339-pulsed dendritic cells supplemented with IL-2, GM-CSF, and 1 tM ibrutinib (to promote Th1 differentiation); and 6) sorted CD4+ T cells from group 5. Size of both flank tumors will be measured thrice weekly on all surviving mice. Three mice per group will be sacrificed three and seven days (or earlier if tumors start to regress) after NEDLI. Cells from spleens, draining LNs and tumor will be analyzed as follows: 1) tumor-specific CD8+ T cells: CD27, CD127, PD-1, KLRG1 expression on p15E specific CD8 T cells and OVA specific T cells (H-2$^{k+}$); 2) Function: Cells will be stimulated separately with M30, p15E peptide, or Class I and II OVA peptides for 5 hours. Frequency of IFN'y-, TNFα-, Granzyme B-, IL-4- and IL-2-producing cells will be analyzed by ICS and flow cytometry; 3) Immunohistochemistry: tumor fragments will be snap frozen in liquid nitrogen. 7 tm tumor sections will be stained with CD4, CD8, p15E tetramer or OVA tetramer along with KLRG-1, PD-1, CD127 or IFN'y; 4) DC activation: Cells from tumor, draining lymph nodes, and spleen will be stained with CD11b, CD11c, Class II, CD70, CD80 and CD86.

Example 15—Materiel and Methods

All the experiments in Examples 13-15 were use on inbred or transgenic mice purchased from Jackson Laboratories or F1 hybrid mice purchased commercially or generated by breeding in house. Mice were be purchased at 6-8 weeks of age and were be approximately 8-10 weeks of age at the initiation of the experiment. Nearly all experiments involved the infusion of cells from a donor strain into tumor-bearing recipients. An equal number of males and females was be used as recipients in each group of mice being treated. The following procedures will be performed:
a) Adoptive cell therapy. Recipient mice were conditioned with either cyclophosphamide 200 mg/kg intraperitoneally or 950 cGy total body irradiation (TBI) one day prior to the intravenous (IV) infusion of lymphocytes via the tail vein. Animals conditioned with TBI were also given T cell-depleted bone marrow cells intravenously to rescue hematopoiesis
b) Mouse Tumor Models—Recipients were challenged with B16-F10 melanoma cells, either 1×10$^5$ IV or 5×10$^5$ subcutaneously (sc), 5×10$^5$ B16-OVA (B16-F10 transfected with the gene for chicken ovalbumin) sc, or 5×10$^4$ TC1 lung cancer cells IV, all two weeks before treatment is commenced.
c) Vaccine—Before immunization, mice received general anesthesia with isoflurane by drop method. Mice will be immunized to synthetic peptide and 50 µg poly (I: C) injecting approximately 200 µl/mouse of the emulsion into the flank. For E7 cDNA vaccine, mice received cDNA (25 µg) intramuscular electroporation (106V, 20-ms pulse at 200-ms intervals for 8 pulses). Mice were checked daily after immunization for evidence of pain and were medicated with buprenorphine SR 0.05 to 0.1 mg/kg sc or ip q 48-72 hrs. as indicated.

Vaccination. C57BL/6×C3H (B6C3) F1 or BALB/c× C57BL/6 (CB6) F1 mice were vaccinated weekly for a total of 3 doses with 25 t g of pcDNA-3-CRT/E71, a DNA vaccine encoding the E7 antigen of the HPV16 serotype. The vaccine was delivered intramuscularly by electroporation with 8 pulses of a 106 V current, each pulse lasting 20 ms with a 200 ms interval between pulses.

Preparation of cells for adoptive immunotherapy. One week following the last vaccination, splenocytes from vaccinated or unvaccinated donors were left untreated or were depleted of CD8+ cells via magnetic cell separation (MACS; Miltenyi Biotec). In experiments using uncultured splenocytes, animals received either 20 million undepleted cells, or CD8-depleted cells containing the number of CD4+ T cells present in 20 million undepleted splenocytes. In some experiments, whole or CD8-depleted splenocytes from vaccinated CB6 F1 donors were cultured with syngeneic CB6 F1 or MHC-haploidentical B6C3 F1 dendritic cells pulsed with 1 µg/ml each of 22 overlapping 15mers from the amino acid sequence of the E7 protein of HPV16 (peptide sequence: MHGDTPTLHE YMLDLQPETT DLYCYEQLND SSEEEDEIDG PAGQAEPDRA HYNIVTFCCK CDSTLRLCVQ STHVDIRTLE DLL-MGTLGIV CPICSQKP; SEQ ID NO: 7) (JPT Technologies). Pentadecapeptides that were adjacent to each other in the E7 sequence overlapped by the C-terminal 11 amino acids. The first four of the 22 peptides are as follows; the remainder may be deduced from the above sequence:

(SEQ ID NO: 8)
MHGDTPTLHEYMLDL (SEQ ID NO: 9)
TPTLHEYMLDLQPET (SEQ ID NO: 10)
HEYMLDLQPETTDLY (SEQ ID NO: 11)
LDLQPETTDLYCYEQ

Dendritic cells were prepared by pan-DC magnetic cell separation (MACS; Miltenyi Biotec). 20 million donor splenocytes were cultured with 2 thousand peptide-pulsed dendritic cells for 5 days in 10 ml RPMI medium supplemented with 10% fetal calf serum, 2-ME, 25 U/ml of recombinant mouse IL-2 and 20 ng/ml recombinant mouse GMCSF. At the end of 5 days, cells were washed and resuspended in phosphate buffered saline. Mice received a dose of ex vivo cultured cells corresponding to an input of the CD4+ T cells contained in 20 million undepleted splenocytes.

Treatment protocol. In experiments testing the anti-tumor efficacy of adoptive cellular therapy, recipient mice were given 5×104 TC1 tumor cells intravenously (IV) via the tail vein on day 0, followed by cyclophosphamide 200 mg/kg intraperitoneally on day 13 and donor cells on day 14. The dose of unstimulated, undepleted donor cells was 20 million spleen cells per recipient. The dose of uncultured, CD8-depleted spleen cells was normalized to contain the same number of CD4+ cells as is contained in 20 million undepleted spleen cells. The dose of ex vivo cultured cells was normalized to the number of CD4+ cells put into culture. As an example, if a mouse spleen contains 100 million total cells and 20 million CD4+ cells, if the CD8-depleted population contains 88 million cells and 18 million CD4+ cells, and if putting 88 million of the CD8-depleted spleen into culture for peptide stimulation results in a stimulated population containing 10 million cells and 4 million CD4+ cells, then the DLI doses would be 20 million whole spleen (contains 4 million CD4+ cells), 19.56 million CD8-depleted spleen (contains 4 million CD4+ cells), or 2.2 million peptide-stimulated cells, Survival of mice in different treatment groups was compared by the Log-Rank test; a p value less than 0.05 was considered significant.

The proposed experiments involve multiple simultaneously occurring cellular interactions resulting in phenomena including graft-versus-host disease (GVHD), anti-tumor effects, and lymphocyte responses to therapeutic vaccination. These complex biological phenomena simply cannot be modeled or reproduced by the in vitro study of lymphocytes. The wide availability of inbred, transgenic, and F1 hybrid strains will allow us to model GVHD and the adoptive immunotherapy of cancer in a clinically relevant way. Specific strains were chosen to model the human situation of HLA-matched sibling or HLA-haploidentical non-engrafting donor lymphocyte infusion (NEDLI). T cell receptor transgenic mice facilitate the tracking of endogenous, tumor-specific T cells in cancer-bearing animals. Also, mouse tumors with defined genetic aberrations leading to chemotherapy resistance, or expressing defined "tumor antigens", are widely available. These experiments can only be done in species such as mice or rats in which inbred and F1 strains are widely available.

After NEDLI and tumor transplants by IV injection through the dorsal tail vein, mice are closely monitored for any tumor related morbidity or toxicities of cell infusion including GVHD (weight loss, hunched posture, ruffled fur, diarrhea, erythema, poor mobility) or cytokine release syndrome (fever, diarrhea, weight loss, immobility). Intravenous injection is only momentarily painful and can be done without anesthesia. Studies are concluded when tumor-free survival in each group has not changed over two weeks of observation. One hundred days of observation following tumor inoculation is usually sufficient for this purpose. This is consistent with recommendations made by the American Veterinary Medical Association (AVMA). Animals are monitored at least thrice weekly following tumor and/or allogeneic lymphocyte infusions for any signs of morbidity from allogeneic GVHD or progressive tumor. As soon as tumor-related morbidity is diagnosed, the tumor-bearing animal is euthanized to prevent undue suffering. Animals in distress from GVHD will also be euthanized.

In experiments in which mice receive subcutaneous injection of tumor, they will generally be euthanized when maximum bi-dimensional measurement of the tumor exceeds 100 mm$^2$, or if the tumor develops extensive ulceration, whichever occurs first. In any experiment, animals that appear to be suffering will be euthanized. Experimental conditions that may lead to suffering include extensive lung metastases producing labored breathing, graft-versus-host disease with significant weight loss, diarrhea, and immobility, or tumor-induced paralysis.

Cell Lines: B16-F10 melanoma (ATCC), B16-OVA melanoma, and TC-1 lung cancer (provided by T C Wu, Johns Hopkins University)

Mouse cell lines will be authenticated by Short Tandem Repeat profiling (National Institute of Standards and Technology Mouse Cell Line Authentication Consortium/American Type Culture Collaboration). Cells will also be tested for *Mycoplasma* Contamination (Genetica Cell Line Testing, Burlington, NC).

Continued expression of the E7 oncogene in TC-1 will be confirmed by PCR using primers for the HPV16 E7 open reading frame.

Upon obtaining B16-F10 from ATCC, cells will be expanded and then 100 aliquots of 1 million cells each will be cryopreserved. A vial of frozen cells will be thawed for each new experiment rather than maintaining cell lines via continuous passaging.

All antibodies for flow cytometry will be purchased from commercial vendors (e.g. BD Biosciences). Antibodies to PD-1 and CTLA-4 for administration to mice are provided by Bio X Cell. Antibody specificity will be confirmed by immunoblot analysis of cell extracts with the target protein overexpressed.

Ibrutinib is provided by Pharmacyclics. We will confirm identity by liquid chromatography-tandem mass spectrometry done by the Johns Hopkins Drug Discovery Core.

Vertebrate Animals: C57BL/6, B6.SJL, BALB/c, C3H, B6×C3H F1, BALB/c×B6 F1, OT-I, and OT-II mouse strains are all purchased from Jackson Laboratories (Bar Harbor, ME). The vendor provides authentication certificates.

Those of skill in the art should, in light of the present disclosure, appreciate that many changes can be made in the specific embodiments which are disclosed and still obtain a like or similar result without departing from the spirit and scope of the invention. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein, will become apparent to those skilled in the art from the foregoing description. Accordingly, the invention is limited only by the following claims.

REFERENCES

1. Ribas A, Wolchok J D. Cancer immunotherapy using checkpoint blockade. Science. 2018; 359(6382):1350-5.
2. Wherry E J, Kurachi M. Molecular and cellular insights into T cell exhaustion. Nat Rev Immunol. 2015; 15(8): 486-99. PMCID: PMC4889009.
3. Alfei F, Zehn D. T Cell Exhaustion: An Epigenetically Imprinted Phenotypic and Functional Makeover. Trends in Molecular Medicine. 2017; 23(9):769-71.
4. Pauken K E, Sammons M A, Odorizzi P M, Manne S, Godec J, Khan O, Drake A M, Chen Z, Sen D, Kurachi M, Barnitz R A, Bartman C, Bengsch B, Huang A C, Schenkel J M, Vahedi G, Haining W N, Berger S L, Wherry E J. Epigenetic stability of exhausted T cells limits durability of reinvigoration by PD-1 blockade. Science. 2016. PMCID: PMC5484795
5. Philip M, Fairchild L, Sun L, Horste E L, Camara S, Shakiba M, Scott A C, Viale A, Lauer P, Merghoub T, Hellmann M D, Wolchok J D, Leslie C S, Schietinger A. Chromatin states define tumour-specific T cell dysfunction and reprogramming. Nature. 2017; 545(7655): PMCID: PMC5693219
6. Ghoneim H E, Fan Y, Moustaki A, Abdelsamed H A, Dash P, Dogra P, Carter R, Awad W, Neale G, Thomas P G, Youngblood B. De Novo Epigenetic Programs Inhibit PD-1 Blockade-Mediated T Cell Rejuvenation. Cell. 2017; 170(1):142-57.e19. PMCID: PMC5568784
7. Arina A, Karrison T, Galka E, Schreiber K, Weichselbaum R R, Schreiber H. Transfer of allogeneic CD4+ T cells rescues CD8+ T cells in anti-PD-L-resistant tumors leading to tumor eradication. Cancer Immunology Research. 2017; 5(2):127-36. PMCID: PMC5354300
8. Symons H J, Levy M Y, Wang J, Zhou X, Zhou G, Cohen S E, Luznik L, Levitsky H I, Fuchs E J. The Allogeneic Effect Revisited: Exogenous Help for Endogenous, Tumor-Specific T Cells. Biology of Blood and Marrow Transplantation. 2008; 14(5):499-509. PMCID: PMC2377414
9. Ridge J P, Di Rosa F, Matzinger P. A conditioned dendritic cell can be a temporal bridge between a CD4+ T-helper and a T-killer cell [see comments]. Nature. 1998; 393 (6684):474-8. PMCID: PMC9624003
10. Bennett S R, Carbone F R, Karamalis F, Flavell R A, Miller J F, Heath W R. Help for cytotoxic-T-cell responses is mediated by CD40 signalling. Nature. 1998; 393 (6684):478-80. PMCID:9624004
11. Schoenberger S P, Toes R E, van der Voort E I, Offringa R, Melief C J. T-cell help for cytotoxic T lymphocytes is mediated by CD40-CD40L interactions. Nature. 1998; 393(6684):480-3. PMCID: PMC9624005
12. Janssen E M, Lemmens E E, Wolfe T, Christen U, von Herrath M G, Schoenberger S P. CD4+ T cells are required for secondary expansion and memory in CD8+ T lymphocytes. Nature. 2003; 421(6925):852-6. PMCID: PMC 12594515
13. Sun J C, Bevan M J. Defective CD8 T cell memory following acute infection without CD4 T cell help. Science. 2003; 300(5617):339-42. PMCID: PMC2778341
14. Shedlock D J, Shen H. Requirement for CD4 T cell help in generating functional CD8 T cell memory. Science. 2003; 300(5617):337-9. PMCID: PMC12690201
15. Zajac A J, Blattman J N, Murali-Krishna K, Sourdive D J, Suresh M, Altman J D, Ahmed R. Viral immune evasion due to persistence of activated T cells without effector function. J Exp Med. 1998; 188(12):2205-13. PMCID: PMC2212420
16. Matloubian M, Concepcion R J, Ahmed R. CD4+ T cells are required to sustain CD8+ cytotoxic T-cell responses during chronic viral infection. J Virol. 1994; 68(12):8056-63. PMCID: PMC237269
17. Keene J A, Forman J. Helper activity is required for the in vivo generation of cytotoxic T lymphocytes. J Exp Med. 1982; 155(3):768-82. PMCID: PMC2186611
18. Aubert R D, Kamphorst A O, Sarkar S, Vezys V, Ha S J, Barber D L, Ye L, Sharpe A H, Freeman G J, Ahmed R. Antigen-specific CD4 T-cell help rescues exhausted CD8 T cells during chronic viral infection. Proceedings of the National Academy of Sciences. 2011; 108(52):21182-7.
19. Ding Z C, Huang L, Blazar B R, Yagita H, Mellor A L, Munn D H, Zhou G. Polyfunctional CD4+ T cells are essential for eradicating advanced B-cell lymphoma after chemotherapy. Blood. 2012; 120(11):2229-39. PMCID: PMC3447781
20. Bachireddy P, Hainz U, Rooney M, Pozdnyakova O, Aldridge J, Zhang W, Liao X, Hodi F S, OGÇÖConnell K, Haining W N, Goldstein N R, Canning C M, Soiffer R J, Ritz J, Hacohen N, Alyea E P, Kim H T, Wu C J. Reversal of in situ T-cell exhaustion during effective human anti-leukemia responses to donor lymphocyte infusion. Blood. 2014; 123(9):1412-21. PMCID: PMD3938152
21. Staveley-O'Carroll K, Sotomayor E, Montgomery J, Borrello I, Hwang L, Fein S, Pardoll D, Levitsky H. Induction of antigen-specific T cell anergy: An early event in the course of tumor progression. Proc Natl Acad Sci USA. 1998; 95(3):1178-83. PMCID: PMC18712
22. Ahrends T, Babala N, Xiao Y, Yagita H, van Eenennaam H, Borst J. CD27 Agonism Plus PD-1 Blockade Recapitulates CD4+ T-cell Help in Therapeutic Anticancer Vaccination. Cancer Res. 2016; 76(10):2921-31.
23. Bevan M J. Helping the CD8+ T-cell response. Nat Rev Immunol. 2004; 4(8):595-602. PMID: 15286726
24. Borst J, Ahrends T, Babala N, Melief C J M, Kastenmuller W. CD4(+) T cell help in cancer immunology and immunotherapy. Nat Rev Immunol. 2018; 18(10): 635-47.
25. Kohrt H E, Müller A, Baker J, Goldstein M J, Newell E, Dutt S, Czerwinski D, Lowsky R, Strober S. Donor immunization with WT1 peptide augments antileukemic activity after MHC-matched bone marrow transplantation. Blood. 2011; 118(19):5319-29. PMCID: PMC3217412.
26. Neelapu S S, Munshi N C, Jagannath S, Watson T M, Pennington R, Reynolds C, Barlogie B, Kwak L W. Tumor antigen immunization of sibling stem cell transplant donors in multiple myeloma. Bone Marrow Transplant. 2005; 36(4):315-23. PMID: PMC15968284
27. Fu H-H, Wang J, Fu J, Jones R J, Levitsky H, Fuchs E J. Tumor Antigen Vaccination of Donors to Augment Graft-Versus-Tumor Effects after Allogeneic Bone Marrow Transplantation with Post-Transplantation Cyclophosphamide. Blood. 2016; 128(22):499-.
28. Strtnen E, Toebes M, Kelderman S, van Buuren M M, Yang W, van Rooij N, Donia M, Bischen M-L, Lund-Johansen F, Olweus J, Schumacher T N. Targeting of cancer neoantigens with donor-derived T cell receptor repertoires. Science. 2016; 352(6291):1337-41. PMCID: PMC27198675.
29. Kreiter S, Vormehr M, van de Roemer N, Diken M, Lower M, Diekmann J, Boegel S, Schrors B, Vascotto F, Castle J C, Tadmor A D, Schoenberger S P, Huber C, Tureci O, Sahin U. Mutant MHC class II epitopes drive therapeutic immune responses to cancer. Nature. 2015; 520(7549):692-6. PMCID: 26040715
30. Ahmadzadeh M, Pasetto A, Jia L, Deniger D C, Stevanovic S, Robbins P F, Rosenberg S A. Tumor-infiltrating human CD4(+) regulatory T cells display a distinct TCR repertoire and exhibit tumor and neoantigen reactivity. Science immunology. 2019; 4(31). PMID: 30635355.
31. Adams A B, Williams M A, Jones T R, Shirasugi N, Durham M M, Kaech S M, Wherry E J, Onami T, Lanier J G, Kokko K E, Pearson T C, Ahmed R, Larsen C P. Heterologous immunity provides a potent barrier to transplantation tolerance. The Journal of Clinical Investigation. 2003; 111(12): 1887-95. PMCID: PMC161424
32. Arina A, Schreiber K, Binder D C, Karrison T G, Liu R B, Schreiber H. Adoptively Transferred Immune T Cells Eradicate Established Tumors despite Cancer-Induced Immune Suppression. The Journal of Immunology. 2014; 192(3):1286-93. doi: 10.4049/jimmunol.1202498. PMCID: PMC4084557.
33. Lehmann P V, Forsthuber T, Miller A, Sercarz E E. Spreading of T-cell autoimmunity to cryptic determinants of an autoantigen. Nature. 1992; 358(6382):155-7.
34. O'Donnell P V, Luznik L, Jones R J, Vogelsang G B, Leffell M S, Phelps M, Rhubart P, Cowan K, Piantados S, Fuchs E J. Nonmyeloablative bone marrow transplantation from partially HLA-mismatched related donors using posttransplantation cyclophosphamide. Biology of Blood and Marrow Transplantation. 2002; 8(7):377-86.
35. SUMNER W C, FORAKER A G. Spontaneous regression of human melanoma: clinical and experimental studies. Cancer. 1960; 13:79-81.
36. Woodruff M F, Nolan B. Preliminary observations on treatment of advanced cancer by injection of allogeneic spleen cells. Lancet. 1963; 13:426-9.
37. Slavin S, Ackerstein A, Or R, Shapira M, Gesundheit B, Askenasy N, Morecki S. Immunotherapy in high-risk chemotherapy-resistant patients with metastatic solid tumors and hematological malignancies using intentionally mismatched donor lymphocytes activated with rIL-2: a phase I study. Cancer Immunol Immunother. 2010; 59(10):1511-9.
38. Medina D J, Gharibo M, Savage P, Cohler A, Kuriyan M, Balsara B, Anand M, Schaar D, Krimmel T, Saggiomo K, Manago J, Talty L, Dudek L, Grospe S, Rubin A, Strair R K. A Pilot study of allogeneic cellular therapy for patients with advanced hematologic malignancies. Leukemia Research. 2008; 32(12):1842-8.
39. Strair R K, Schaar D, Medina D, Todd M B, Aisner J, DiPaola R S, Manago J, Knox B, Jenkinson A, Senzon R, Baker C, Dudek L, Ciardella M, Kuriyan M, Rubin A, Lattime E C. Antineoplastic Effects of Partially HLA-Matched Irradiated Blood Mononuclear Cells in Patients With Renal Cell Carcinoma. Journal of Clinical Oncology. 2003; 21(20):3785-91.
40. Schwarzenberg L, Mathe G, Schneider M, Amiel J L, Cattan A, Schlumberger J R. Attempted adoptive immunotherapy of acute leukaemia by leucocyte transfusions. Lancet. 1966; 2(459):365-8.
41. Colvin G A, Berz D, Ramanathan M, Winer E S, Fast L, Elfenbein G J, Quesenberry P J. Nonengraftment Haploidentical Cellular Immunotherapy for Refractory Malignancies: TumoriResponses without Chimerism. Biology of Blood and Marrow Transplantation. 2009; 15(4):421-31.
42. Ballen K K, Becker P S, Emmons R V B, Fitzgerald T J, Hsieh C C, Liu Q, HEYES C, Clark Y, Levy W, LAMBERT J F. Low-dose total body irradiation followed by allogeneic lymphocyte infusion may induce remission in patients with refractory hematologic malignancy. Blood. 2002; 100(2):442-50.
43. Kondo M, McCarty M F. Rationale for a novel immunotherapy of cancer with allogeneic lymphocyte infusion. Med Hypotheses. 1984; 15(3):241-77.
44. Alexander P, Delorme E J, Hall J G. The effect of lymphoid cells from the lymph of specifically immunized sheep on the growth of primary sarcomata in rats. Lancet 1966. p. 1186-9.
45. Guo M, Hu K X, Yu C L, Sun Q Y, Qiao J H, Wang D H, Liu G X, Sun W J, Wei L, Sun X D, Huang Y J, Qiao J X, Dong Z, Ai H S. Infusion of HLA-mismatched peripheral blood stem cells improves the outcome of chemotherapy for acute myeloid leukemia in elderly patients. Blood. 2011; 117(3):936-41.
46. Dubovsky J A, Beckwith K A, Natarajan G, Woyach J A, Jaglowski S, Zhong Y, Hessler J D, Liu T M, Chang B Y, Larkin K M, Stefanovski M R, Chappell D L, Frissora F W, Smith L L, Smucker K A, Flynn J M, Jones J A, Andritsos L A, Maddocks K, Lehman A M, Furman R, Sharman J, Mishra A, Caligiuri M A, Satoskar A R, Buggy J J, Muthusamy N, Johnson A J, Byrd J C. Ibrutinib is an irreversible molecular inhibitor of ITK driving a Th1-selective pressure in T lymphocytes. Blood. 2013; 122 (15):2539-49. PMCID: PMC3795457.
47. Willimsky G, Blankenstein T. Sporadic immunogenic tumours avoid destruction by inducing T-cell tolerance. Nature. 2005; 437(7055):141-6.
48. Castle J C, Kreiter S, Diekmann J, L+|wer M, van de Roemer N, de Graaf J, Selmi A, Diken M, Boegel S, Paret C, Koslowski M, Kuhn A N, Britten C M, Huber C, Türeci O, Sahin U. Exploiting the Mutanome for Tumor Vaccination. Cancer Research. 2012; 72(5):1081-91.
49. Bos R, Sherman L A. CD4+ T-Cell Help in the Tumor Milieu Is Required for Recruitment and Cytolytic Function of CD8+ T Lymphocytes. Cancer Research. 2010; 70(21):8368-77. PMCID: PMC2970736.
50. Wong S B J, Bos R, Sherman L A. Tumor-Specific CD4+ T Cells Render the Tumor Environment Permissive for Infiltration by Low-Avidity CD8+ T Cells. The Journal of Immunology. 2008; 180(5):3122-31.
51. Heusinkveld M, de Vos van Steenwijk P, Goedemans R, Ramwadhdoebe T H, Gorter A, Welters M J P, van Hall T, van der Burg S H. M2 Macrophages Induced by Prostaglandin E2 and IL-6 from Cervical Carcinoma Are Switched to Activated M1 Macrophages by CD4+ Th1 Cells. The Journal of Immunology. 2011; 187(3):115765.
52. Feau S, Garcia Z, Arens R, Yagita H, Borst J, Schoenberger S P. The CD4+ T-cell help signal is transmitted from APC to CD8+ T-cells via CD27Gc8CD70 interactions. Nat Commun. 2012; 3:948. PMCID: PMC3606886
53. Singh M, Vianden C, Cantwell M J, Dai Z, Xiao Z, Sharma M, Khong H, Jaiswal A R, Faak F, Hailemichael Y, Janssen L M E, Bharadwaj U, Curran M A, Diab A, Bassett R L, Tweardy D J, Hwu P, Overwijk W W. Intratumoral CD40 activation and checkpoint blockade induces T cell-mediated eradication of melanoma in the brain. Nat Commun. 2017; 8(1):1447. PMCID: PMC5682289.
54. Zeh H J, 3rd, Perry-Lalley D, Dudley M E, Rosenberg S A, Yang J C. High avidity CTLs for two self-antigens demonstrate superior in vitro and in vivo antitumor efficacy. J Immunol. 1999; 162(2):989-94 PubMed PMID: 9916724.
55. Hayashi H, Matsubara H, Yokota T, Kuwabara I, Kanno M, Koseki H, Isono K, Asano T, Taniguchi M. Molecular cloning and characterization of the gene encoding mouse melanoma antigen by cDNA library transfection. J Immunol. 1992; 149(4):1223-9. Epub 1992/08/15. PubMed PMID: 1380036.
56. Bachireddy P, Hainz U, Rooney M, Pozdnyakova O, Aldridge J, Zhang W, Liao X, Hodi F S, O'Connell K, Haining W N, Goldstein N R, Canning C M, Soiffer R J, Ritz J, Hacohen N, Alyea E P, Kim H T, Wu C J. Reversal of in situ T cell exhaustion during effective human anti-leukemia responses to donor lymphocyte infusion. Blood. 2013. PMCID: PMC3938152
57. Verbeke G, Molenberghs G. Linear mixed models for longitudinal data: Springer Science & Business Media; 2009. ISBN 978-0-387-22775-7
58. Littell R C, Milliken G A, Stroup W W, Wolfinger R D, Schabenberger O. SAS for mixed models: SAS institute Cary, NC; 2006.
59. Westfall P H, Young S S. Resampling-based multiple testing: Examples and methods for p-value adjustment: John Wiley & Sons; 1993. ISBN: 978-O-471-55761-6
60. Liu C, Cripe T P, Kim M-O. Statistical issues in longitudinal data analysis for treatment efficacy studies in the biomedical sciences. Molecular therapy: the journal of the American Society of Gene Therapy. 2010; 18(9):1724-30. PMC2956920
61. Jiménez-Sánchez A, Memon D, Pourpe S, Veeraraghavan H, Li Y, Vargas H A, Gill M B, Park K J, Zivanovic O, Konner J, Ricca J, Zamarin D, Walther T, Aghajanian C, Wolchok J D, Sala E, Merghoub T, Snyder A, Miller M L. Heterogeneous Tumor-Immune Microenvironments among Differentially Growing Metastases in an Ovarian Cancer Patient. Cell. 2017; 170(5):927-38.e20. PMCID: PMC5589211
62. McGranahan N, Rosenthal R, Hiley C T, Rowan A J, Watkins T B K, Wilson G A, Birkbak N J, Veeriah S, Van Loo P, Herrero J, Swanton C. Allele-Specific HLA Loss and Immune Escape in Lung Cancer Evolution. Cell. 2017; 171(6):1259-71.ell. PMC5720478.
63. Riaz N, Havel J J, Makarov V, Desrichard A, Urba W J, Sims J S, Hodi F S, Martin-Algarra S, Mandal R, Sharfman W H, Bhatia S, Hwu W J, Gajewski T F, Slingluff C L, Jr., Chowell D, Kendall S M, Chang H, Shah R, Kuo F, Morris L G T, Sidhom J W, Schneck J P, Horak C E, Weinhold N, Chan T A. Tumor and Microenvironment Evolution during Immunotherapy with Nivolumab. Cell. 2017. PubMed PMID: 29033130. PMC5685550
64. Hogquist K A, Jameson S C, Heath W R, Howard J L, Bevan M J, Carbone F R. T cell receptor antagonist peptides induce positive selection. Cell. 1994; 76(1):17-27. PMC5685550
65. Barnden M J, Allison J, Heath W R, Carbone F R. Defective TCR expression in transgenic mice constructed using cDNA-based alpha- and beta-chain genes under the control of heterologous regulatory elements. Immunol Cell Biol. 1998; 76(1):34-40. PMID: 9553774.
66. Cheng W-F, Hung C-F, Chai C-Y, et al. Tumor-specific immunity and antiangiogenesis generated by a DNA vaccine encoding calreticulin linked to a tumor antigen. The Journal of Clinical Investigation 2001; 108:669-78.

What is claimed is:

1. A method of making a lymphocyte composition for administration to a recipient comprising:
   a) obtaining a peripheral blood cell composition from a donor, wherein the donor is vaccinated against an antigen present in the recipient, and wherein the peripheral blood cell composition contains CD8+ T-cells, CD4+ T-cells, and natural killer cells;
   b) depleting the peripheral blood cell composition of the CD8+ T-cells, wherein depleting the peripheral blood cell composition of the CD8+ T-cells is reducing the number of CD8+ T-cells in the peripheral blood cell composition by at least one order of magnitude; and
   c) expanding the CD4+ T cells specific to the antigen by culturing the CD4+ T cells with the antigen,
wherein the donor is partially HLA-mismatched, or HLA-haploidentical to the recipient, thereby making a lymphocyte composition.

2. The method of claim 1, wherein the antigen is selected from the group consisting of a neoplastic antigen, a neoplastic idiotype, a viral antigen, a bacterial antigen, a fungal antigen, a parasitic antigen, a non-human animal antigen, a tumor neoantigen, and a combination thereof.

3. The method of claim 2, wherein the viral antigen is selected from the group consisting of a human papillomavirus (HPV) E6 antigen, a HPV E7 antigen and a combination thereof.

4. The method of claim 2, wherein the viral antigen is selected from the group consisting of an Epstein-Barr virus latent membrane protein 1 (LMP1), a latent membrane protein 2a (LMP 2a) and a combination thereof.

5. The method of claim 2, wherein the antigen is a neoplastic antigen or a tumor neoantigen.

6. The method of claim 5, wherein the tumor neoantigen is an antigen from a recipient's tumor.

7. The method of claim 1, wherein the donor is a cancer-free donor.

8. The method of claim 1, wherein the partially HLA-mismatched or HLA-haploidentical donor has at least one human leukocyte antigen (HLA) Class II allele match relative to the recipient and the HLA Class II allele match is at a gene selected from the group consisting of HLA-DRB1, HLA-DQB1, and HLA-DPB1.

9. The method of claim 8, wherein the donor has at least one HLA Class II allele mis-match relative to the recipient in the donor anti-recipient (graft-versus-host direction) and the HLA Class II allele mis-match is at a gene selected from the group consisting of HLA-DRB1, HLA-DQB1, and HLA-DPB1.

10. The method of claim 1, wherein a donor vaccinated against an antigen present in the recipient is a donor having CD4+ T-cell immunity against the antigen present in the recipient.

11. The method of claim 1, wherein the recipient does not have detectable antibodies reactive against human leukocyte antigens of the donor.

12. The method of claim 1, wherein reducing the CD8+ T-cells in the peripheral blood cell composition comprises using an anti-CD8+ antibody associated with magnetic particles or an anti-CD8+ antibody plus complement.

13. The method of claim 1, wherein a subject selected from the group consisting of the recipient, the donor and one or more potential allogeneic donor(s) has been screened for serological reactivity to an infectious agent antigen selected from the group consisting of a Human Immunodeficiency Virus (HIV) antigen, a Hepatitis Virus antigen, Epstein-Barr virus and a Cytomegalovirus antigen.

14. The method of claim 1, wherein the number of CD4+ T-cells in the allogeneic lymphocyte composition differs from the number of CD4+ T-cells in the peripheral blood cell composition by less than about 50%.

15. The method of claim 1, wherein the number of donor CD4+ T-cells based on an ideal body weight of the recipient in kilograms (kg) is between about $1\times10^5$ CD4+ T-cells/kg and about $1\times10^9$ CD4+ T-cells/kg.

16. The method of claim 1, further comprising depleting the peripheral blood cell composition of at least one additional cell type selected from natural killer (NK) cells and regulatory T cells (Tregs), wherein depleting the peripheral blood cell composition of at least one additional cell type is reducing the number of NK cells and/or the number of Tregs in the peripheral blood cell composition by at least one order of magnitude.

17. The method of claim 16, wherein the Tregs are CD4+ CCD25+ regulatory T cells.

18. The method of claim 16, wherein depleting the peripheral blood cell composition of at least one additional cell type selected from NK cells and Tregs comprises depleting the peripheral blood cell composition of NK cells and Tregs.

19. The method of claim 1, further comprising polarizing the donor with cytokines to enrich the blood cell composition for interferon gamma producing T cells or interleukine-17 producing CD4+ T cells.

\* \* \* \* \*

SEQUENCE LISTING

```
<160> NUMBER OF SEQ ID NOS: 11

<210> SEQ ID NO 1
<211> LENGTH: 27
<212> TYPE: PRT
<213> ORGANISM: Artificial Sequence
<220> FEATURE:
<223> OTHER INFORMATION: Synthetic

<400> SEQUENCE: 1

Pro Ser Lys Pro Ser Phe Gln Glu Phe Val Asp Trp Glu Lys Val Ser
1               5                   10                  15

Pro Glu Leu Asn Ser Thr Asp Gln Pro Phe Leu
            20                  25

<210> SEQ ID NO 2
<211> LENGTH: 27
<212> TYPE: PRT
<213> ORGANISM: Artificial Sequence
<220> FEATURE:
<223> OTHER INFORMATION: Synthetic

<400> SEQUENCE: 2

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Ser Ile Ile Asn Phe Glu Lys Leu
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Ile Ser Gln Ala Val His Ala Ala His Ala Glu Ile Asn Glu Ala Gly
1               5                   10                  15

Arg
```

-continued

```
<210> SEQ ID NO 5
<211> LENGTH: 27
<212> TYPE: PRT
<213> ORGANISM: Artificial Sequence
<220> FEATURE:
<223> OTHER INFORMATION: Synthetic

<400> SEQUENCE: 5

Pro Ser Lys Pro Ser Phe Gln Glu Phe Val Asp Trp Glu Lys Val Ser
1               5                   10                  15

Pro Glu Leu Asn Ser Thr Asp Gln Pro Phe Leu
            20                  25

<210> SEQ ID NO 6
<211> LENGTH: 27
<212> TYPE: PRT
<213> ORGANISM: Artificial Sequence
<220> FEATURE:
<223> OTHER INFORMATION: Synthetic

<400> SEQUENCE: 6

Pro Ser Lys Pro Ser Phe Gln Glu Phe Val Asp Trp Glu Asn Val Ser
1               5                   10                  15

Pro Glu Leu Asn Ser Thr Asp Gln Pro Phe Leu
            20                  25

<210> SEQ ID NO 7
<211> LENGTH: 98
<212> TYPE: PRT
<213> ORGANISM: Artificial Sequence
<220> FEATURE:
<223> OTHER INFORMATION: Synthetic

<400> SEQUENCE: 7

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu Asp Glu Ile Asp Gly Pro Ala Gly Gln Ala Glu Pro Asp
        35                  40                  45

Arg Ala His Tyr Asn Ile Val Thr Phe Cys Cys Lys Cys Asp Ser Thr
    50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 8
<211> LENGTH: 15
<212> TYPE: PRT
<213> ORGANISM: Artificial Sequence
<220> FEATURE:
<223> OTHER INFORMATION: Synthetic

<400> SEQUENCE: 8

Met His Gly Asp Thr Pro Thr Leu His Glu Tyr Met Leu Asp Leu
1               5                   10              15

<210> SEQ ID NO 9
<211> LENGTH: 15
<212> TYPE: PRT
<213> ORGANISM: Artificial Sequence
```

```
<220> FEATURE:
<223> OTHER INFORMATION: Synthetic

<400> SEQUENCE: 9

Thr Pro Thr Leu His Glu Tyr Met Leu Asp Leu Gln Pro Glu Thr
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Synthetic

<400> SEQUENCE: 10

His Glu Tyr Met Leu Asp Leu Gln Pro Glu Thr Thr Asp Leu Tyr
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Synthetic

<400> SEQUENCE: 11

Leu Asp Leu Gln Pro Glu Thr Thr Asp Leu Tyr Cys Tyr Glu Gln
1               5                   10                  15
```